US011247061B2

(12) United States Patent
Thompson-Nauman et al.

(10) Patent No.: US 11,247,061 B2
(45) Date of Patent: Feb. 15, 2022

(54) CARDIAC DEVICE SYSTEM

(71) Applicant: Medtronic, Inc., Minneapolis, MN (US)

(72) Inventors: Amy E. Thompson-Nauman, Ham Lake, MN (US); Jeffrey D. Wilkinson, Vadnais Heights, MN (US); Darrell J. Swenson, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/536,979

(22) Filed: Aug. 9, 2019

(65) Prior Publication Data
US 2020/0046989 A1 Feb. 13, 2020

Related U.S. Application Data

(60) Provisional application No. 62/716,863, filed on Aug. 9, 2018.

(51) Int. Cl.
*A61N 1/39* (2006.01)
(52) U.S. Cl.
CPC ......... *A61N 1/3987* (2013.01); *A61N 1/3956* (2013.01)
(58) Field of Classification Search
CPC .. A61N 1/3987; A61N 1/3956; A61N 1/3925; A61N 1/36535; A61B 5/1116; A61M 2230/202; A61M 2230/432; A61M 2230/433; A61M 2016/0413
See application file for complete search history.

(56) References Cited

U.S. PATENT DOCUMENTS

| 5,607,455 A | 3/1997 | Armstrong |
| 5,954,752 A | 9/1999 | Mongeon et al. |
| 7,130,687 B2 | 10/2006 | Cho et al. |
| 7,643,877 B2 | 1/2010 | Dujmovic, Jr. et al. |
| 7,972,276 B1 | 7/2011 | Min |
| 8,708,934 B2 | 4/2014 | Skelton et al. |

(Continued)

FOREIGN PATENT DOCUMENTS

| WO | 2013186560 A1 | 12/2013 |
| WO | 2018026481 A1 | 2/2018 |

OTHER PUBLICATIONS

International Search Report and Written Opinion of International Application No. PCT/US2019/045925, dated Nov. 12, 2019, 14 pp.
(Continued)

*Primary Examiner* — Carl H Layno
*Assistant Examiner* — Anh-Khoa N Dinh
(74) *Attorney, Agent, or Firm* — Shumaker & Sieffert, P.A.

(57) ABSTRACT

In some examples, medical device systems that deliver anti-tachyarrhythmia shock(s) (e.g., defibrillation shock(s)) to a heart of a patient in coordination with the respiration of the patient. In one example, a medical device system including therapy generation circuitry configured to generate a defibrillation shock. The medical device system also includes processing circuitry configured to identify a time at which a respiratory volume of a lung of a patient is at approximately end tidal volume or less; and control the therapy generation circuitry to deliver the defibrillation shock to a heart of the patient at the time that the respiratory volume of the lung of a patient is at the approximately end tidal volume or less.

26 Claims, 14 Drawing Sheets

(56) References Cited

U.S. PATENT DOCUMENTS

| | | | |
|---|---|---|---|
| 2002/0082658 A1* | 6/2002 | Heinrich | A61N 1/3918 607/9 |
| 2003/0045910 A1 | 3/2003 | Sorenson et al. | |
| 2003/0139780 A1 | 7/2003 | Markowitz et al. | |
| 2003/0212436 A1* | 11/2003 | Brown | A61N 1/3629 607/5 |
| 2005/0096703 A1 | 5/2005 | Sanders | |
| 2005/0209647 A1 | 9/2005 | Wanasek et al. | |
| 2006/0167502 A1 | 7/2006 | Haefner | |
| 2007/0179539 A1 | 8/2007 | Degroot et al. | |
| 2007/0225623 A1* | 9/2007 | Freeman | A61N 1/3987 601/41 |
| 2008/0188901 A1 | 8/2008 | Sanghera et al. | |
| 2008/0194980 A1* | 8/2008 | Gisolf | A61B 5/029 600/526 |
| 2009/0005827 A1 | 1/2009 | Weintraub et al. | |
| 2010/0010391 A1 | 1/2010 | Skelton et al. | |
| 2011/0098775 A1 | 4/2011 | Allavatam et al. | |
| 2011/0112419 A1* | 5/2011 | Bjorling | A61B 5/363 600/509 |
| 2011/0201945 A1 | 8/2011 | Li et al. | |
| 2012/0109244 A1* | 5/2012 | Anderson | A61N 1/36521 607/17 |
| 2012/0259183 A1 | 10/2012 | Thakur et al. | |
| 2013/0289649 A1 | 10/2013 | Averina et al. | |
| 2014/0277256 A1 | 9/2014 | Osorio | |
| 2014/0330326 A1 | 11/2014 | Thompson-Nauman et al. | |
| 2015/0297903 A1* | 10/2015 | Kantor | A61M 15/009 128/200.23 |
| 2016/0000350 A1 | 1/2016 | Zhang | |
| 2016/0144192 A1* | 5/2016 | Sanghera | A61N 1/059 607/18 |
| 2017/0027527 A1* | 2/2017 | Bhat | A61B 5/7275 |
| 2017/0157395 A1 | 6/2017 | Thompson-Nauman et al. | |
| 2017/0245794 A1 | 8/2017 | Sharma et al. | |
| 2017/0296086 A1 | 10/2017 | Ternes et al. | |
| 2018/0021570 A1 | 1/2018 | An et al. | |
| 2018/0035898 A1 | 2/2018 | Gunderson | |
| 2018/0177425 A1 | 6/2018 | Stadler et al. | |

OTHER PUBLICATIONS

U.S. Appl. No. 16/537,025, filed Aug. 9, 2019, by Wilkinson et al.

Shin et al., "Rate-adaptive pacemaker controlled by motion and respiratory rate using neuro-fuzzy algorithm," Medical & Biological Engineering & Computing, vol. 39, Jul. 3, 2001, 6 pp.

Baudoin et al.,"The superior epigastric artery does not pass through Larrey's space (trigonum sternocostale)," Surgical & Radiologic Anatomy, Springer, published online Aug. 1, 2003, 5 pp.

Wilkinson et al., "Extravascular sensed signal amplitude variability due to posture and respiration: insights from posture specific modeling in a highly automated electrophysiological modeling environment," Best Posters in heart and vascular development / Best Posters in computer modelling and simulation, published Aug. 28, 2018, 1 pp.

International Preliminary Report on Patentability from International Application No. PCT/US2019/045925, dated Feb. 18, 2021, 8 pp.

* cited by examiner

CARDIAC DEVICE SYSTEM

This application claims the benefit of U.S. Provisional Patent Application No. 62/716,863, filed Aug. 9, 2018, the entire content of which is incorporated by reference herein.

TECHNICAL FIELD

The disclosure generally relates to cardiac device systems, such as an implantable cardiac device system configured to deliver anti-tachyarrhythmia therapy.

BACKGROUND

For patients at risk of tachyarrhythmias, such as ventricular fibrillation (VF) and/or non-perfusing ventricular tachycardia (VT), an implantable cardiac device system, such as an implantable cardioverter defibrillator (ICD) system, may be used to delivery anti-tachyarrhythmia therapy to a heart of the patient. An ICD system may include an electrical housing electrode (sometimes referred to as a can electrode) that is coupled to one or more electrical lead wires placed within the heart. If an arrhythmia is sensed, the ICD may send a pulse via the electrical lead wires to shock the heart and restore its normal rhythm. In some examples, rather than placing and attaching electrical leads directly within the heart of a patient, extravascular ICD systems have been devised to provide shocks to the heart without placing electrical lead wires within the heart.

SUMMARY

Aspects of the disclosure are directed to medical device systems, such as ICD systems, configured to coordinate delivery of anti-tachyarrhythmia therapy (e.g., in the form of defibrillation shock(s) or cardioversion shock(s)) to a patient with respiration of the lungs of a patient. For example, the ICD system may be in the form of an extravascular implantable cardiac device configured to determine a time when one or both lungs of a patient are at approximately end tidal volume or less, and then deliver anti-tachyarrhythmia shocks (e.g., one or more defibrillation shocks) to the heart of a patient when the respiratory volume of the one or both lungs is at approximately tidal volume or less to treat, e.g., VF or VT of the heart. For example, an ICD system may coordinate the delivery of one or more defibrillation shocks such that the shocks are delivered substantially coincidentally with approximately an end of exhalation by a patient, as determined by the ICD system.

In some instances, timing the delivery of anti-tachyarrhythmia shock(s) in coordination with the respiration and respiratory volume of the lung(s) of the patient in such a manner may allow for defibrillation of the heart of a patient at a lower threshold (e.g., as compared to anti-tachyarrhythmia shock(s) delivered when the lung(s) respiratory capacity is at or near maximum tidal volume), resulting in less electroporation and/or troponin release. Additionally or alternatively, timing the delivery of defibrillation shock(s) in coordination with the respiration and respiratory volume of the lung(s) of the patient in such a manner may allow for a relatively higher defibrillation efficacy rate for a shock having an energy amount, e.g., as compared to the efficacy of a defibrillation shock having the same amount of energy but delivered when the lung(s) respiratory capacity is at or near maximum tidal volume.

In examples, the disclosure is directed to a method comprising identifying a time at which a respiratory volume of a lung of a patient is at approximately end tidal volume or less; and delivering, via a medical device system, an anti-tachyarrhythmia shock to a heart of the patient at the time that the respiratory volume of the lung of a patient is at the approximately end tidal volume or less.

In another example, the disclosure is directed to a medical device system comprising therapy generation circuitry configured to generate an anti-tachyarrhythmia shock; and processing circuitry configured to identify a time at which a respiratory volume of a lung of a patient is at approximately end tidal volume or less; and control the therapy generation circuitry to deliver the anti-tachyarrhythmia shock to a heart of the patient at the time that the respiratory volume of the lung of a patient is at the approximately end tidal volume or less.

This summary is intended to provide an overview of the subject matter described in this disclosure. It is not intended to provide an exclusive or exhaustive explanation of the systems, devices, and methods described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1A:
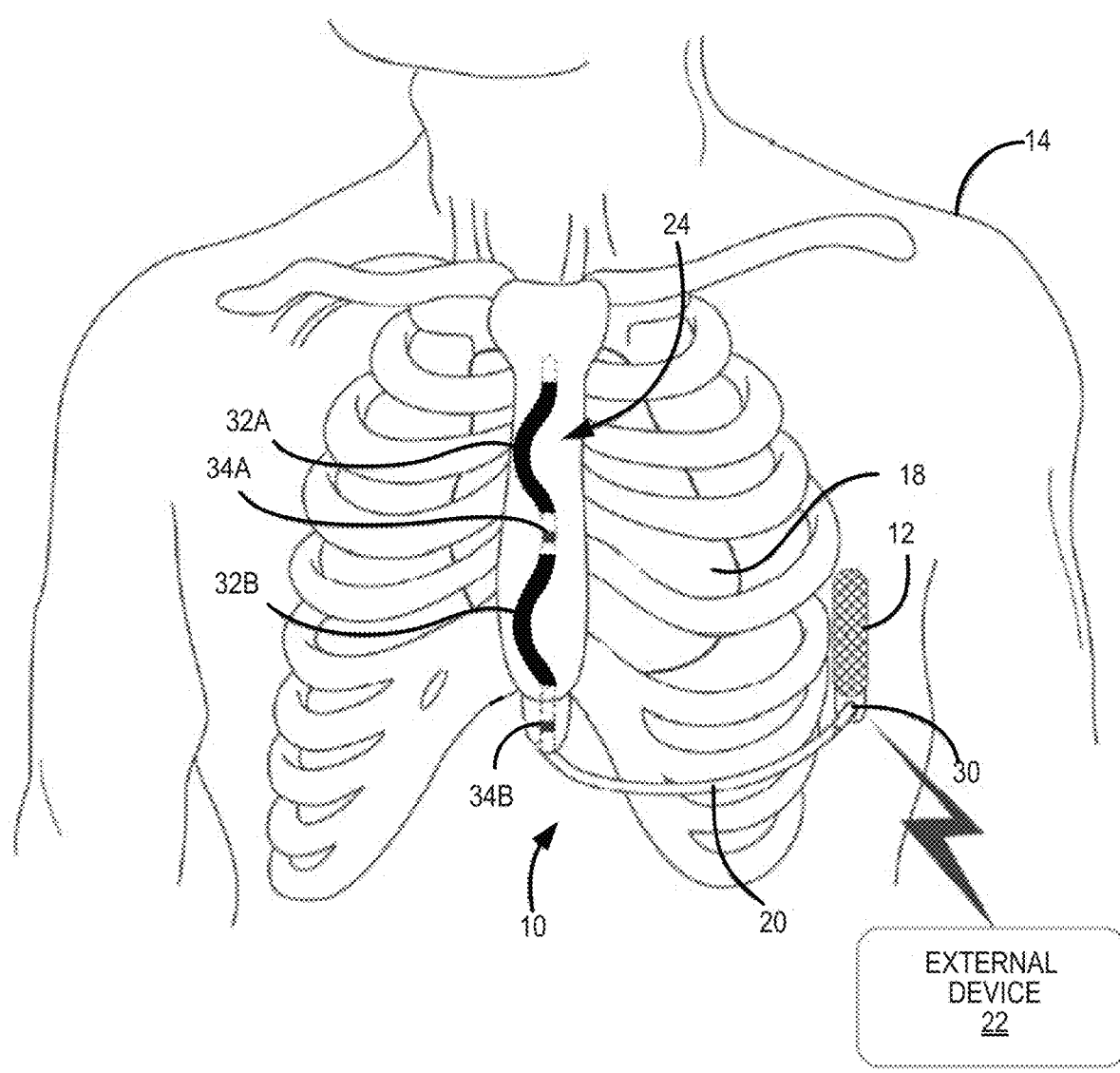
FIGS. 1A-1C are front-view, side-view, and top-view conceptual drawings, respectively, illustrating an example medical device system in conjunction with a patient.

Aspects of this disclosure relate to methods and systems for delivering anti-tachyarrhythmia therapy to the heart of a patient in coordination with the respiration cycle of the patient. As noted above, in some examples, the disclosure is directed an ICD system in the form of an extravascular implantable cardiac device that may be configured to determine the relative respiratory volume of a patient's lung(s) (e.g., by monitoring inhalation and exhalation of the patient), and deliver one or more defibrillation shocks to the heart of a patient when the lung(s) have a respiratory volume that is at approximately tidal volume or less to treat, e.g., VF or VT of the heart. In some instances, such coordination may result in withholding the delivery of anti-tachyarrhythmia therapy to the heart of a patient for some period of time after the detecting the VF or VT of the heart until a time in which the lung's respiratory volume of the patient is at approximately tidal volume or less. For example, an ICD system may detect the VF or VT of the heart at the same time the patient is near the end of inhalation (breathing in) of air during normal resting respiration. In such a scenario, the ICD system may withhold the delivery of anti-tachyarrhythmia therapy (e.g., the delivery of one or more defibrillation shocks) to the heart of the patient until a time at which the respiratory volume of the lungs of the patient is at approximately tidal volume or less, e.g., at the end of the next exhalation of air following the preceding inhalation.

In some examples, the ICD system may coordinate the delivery of the anti-tachyarrhythmia therapy with a posture of a patient in addition to the respiratory volume of the lung(s) of the patient. For example, following the detection of VF or VT of the heart of a patient by an ICD system, the ICD system may time the delivery of anti-tachyarrhythmia shock(s) such that the shock(s) are delivered at a time in which the patient's respiratory volume is at approximately tidal volume or less (e.g., at approximately the end of exhalation by the patient) and the patient occupies a target posture (e.g., when the patient is in a supine posture or other lying posture as compared to a upright/standing posture or reclined posture). Such an example may again allow for a lower DFT and/or more therapeutically effective defibrillation for a given shock energy, e.g., as compared to delivering the anti-tachyarrhythmia shock(s) when the patient does not occupy the target posture in addition to the patient being at approximately end tidal volume or less.

For ease of description, examples of the disclosure are described primarily in the context of coordinating the delivery of anti-tachyarrhythmia therapy (e.g., shock(s)) with the respiration of a patient in the form of the delivery of one or more defibrillation shocks in coordination with the respiration of the patient. However, examples of anti-tachyarrhythmia therapy are not limited to the delivery of defibrillation shock(s). For example, in some instances, the anti-tachyarrhythmia therapy delivered to the patient may be in the form of one or more of cardioversion shock(s), antitachycardia pacing (ATP), post shock pacing, bradycardia pacing, or other suitable therapy to the heart, e.g., to VF or VT of the heart.

Figure 1B:
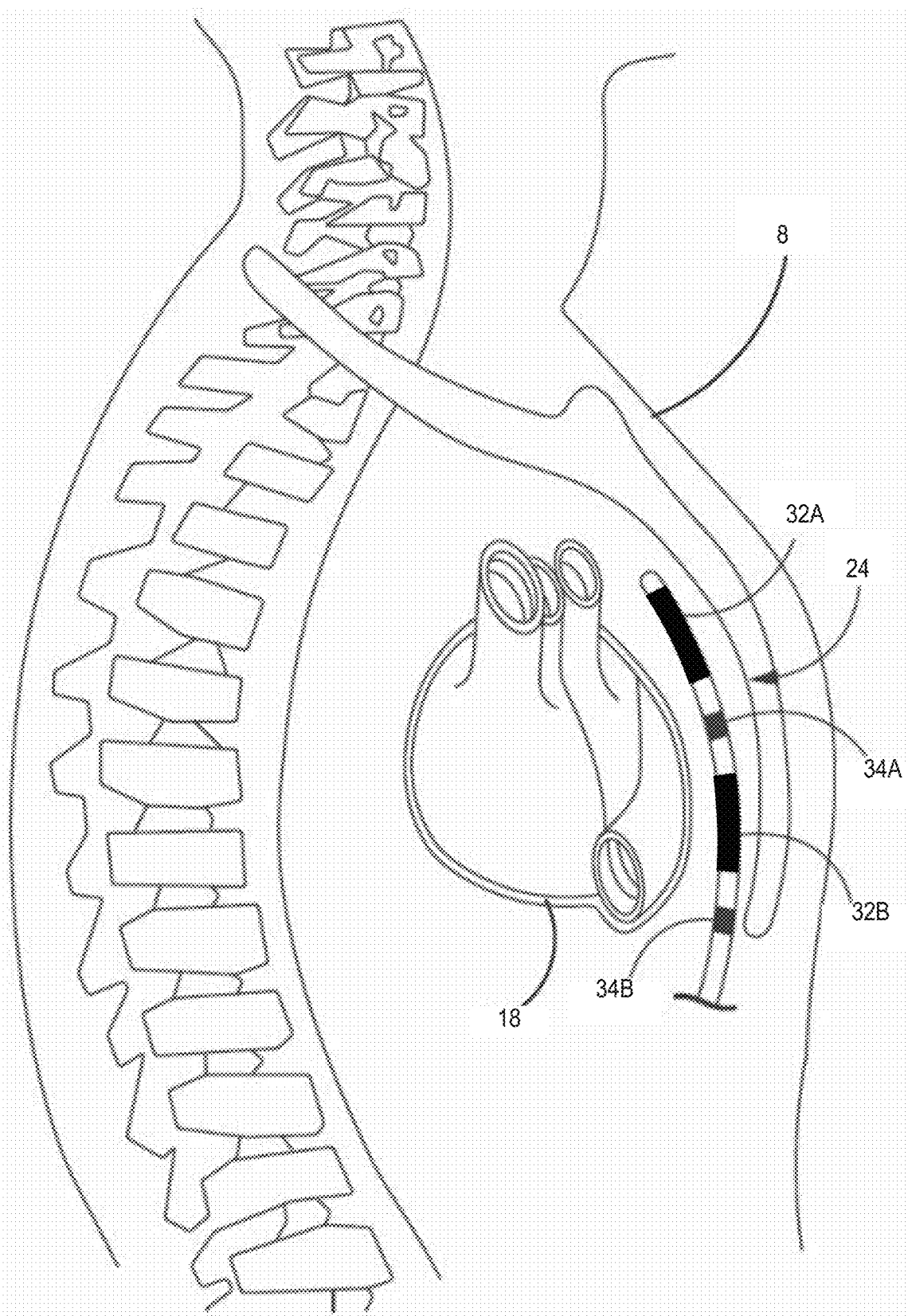
Figure 1C:
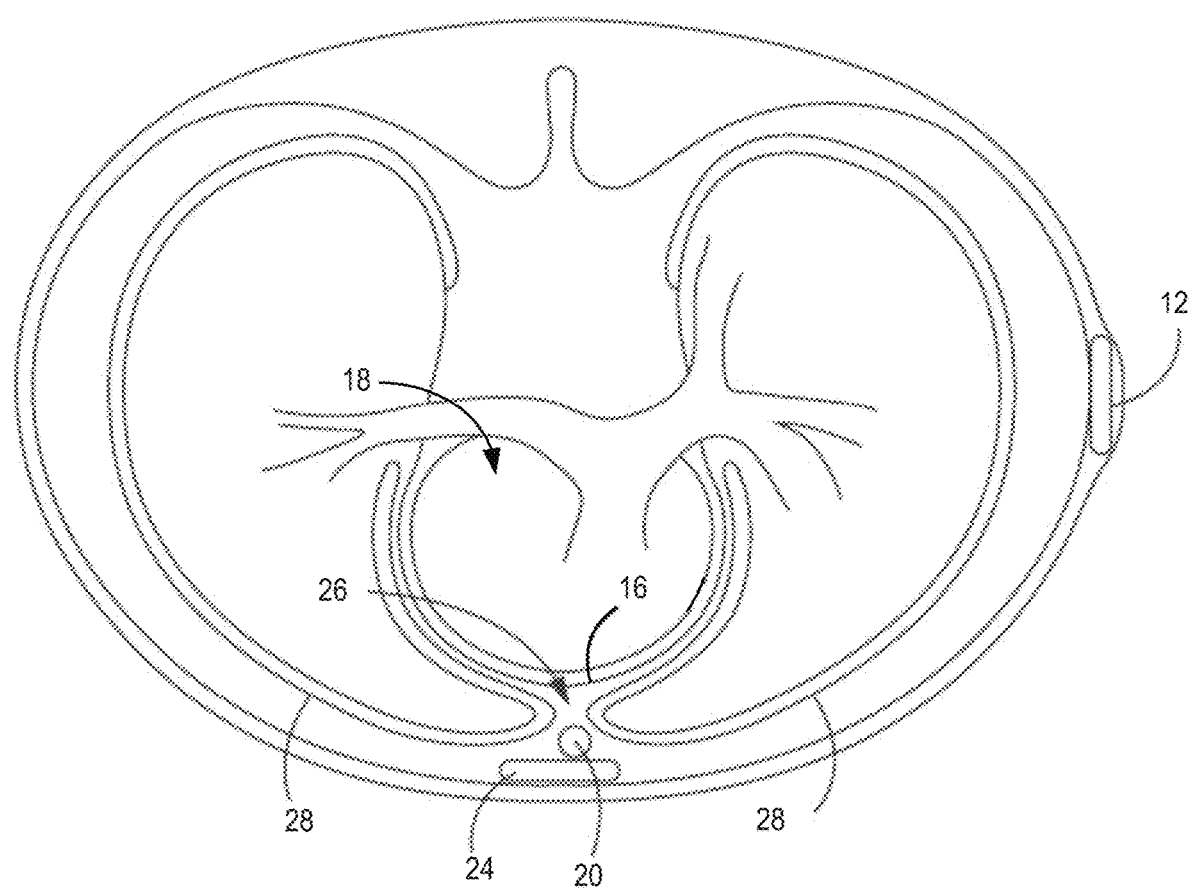

FIGS. 1A-1C are front-view, side-view, and top-view conceptual drawings, respectively, illustrating an example of medical device system 10 (also referred to as "system 10") in conjunction with patient 14. In the illustrated example, the medical device system 10 is an extracardiovascular implantable cardioverter defibrillator (ICD) system implanted within patient 14. However, the described systems and techniques may be applicable to other cardiac systems, including cardiac pacemaker systems, cardiac resynchronization therapy defibrillator (CRT-D) systems, cardioverter systems, or combinations thereof. In addition, system 10 may not be limited to treatment of a human patient. In alternative examples, system 10 may be implemented in non-human patients, such as primates, canines, equines, pigs, bovines, ovines, felines, or the like. These other animals may undergo clinical or research therapies that may benefit from the subject matter of this disclosure.

Medical device system may include one or more medical devices, leads, external devices, or other components configured for the techniques described herein. In the illustrated example, system 10 includes an implantable medical device (IMD) 12, which may be an ICD. IMD 12 is connected to at least one implantable cardiac defibrillation lead 20. In some examples, two leads or more than two leads are used. IMD 12 may be configured to deliver high-energy cardioversion or defibrillation pulses to a patient's heart 18 when a ventricular tachyarrhythmias, e.g., ventricular tachycardia (VT) or ventricular fibrillation (VF), is detected. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by IMD 12.

IMD 12 may be implanted subcutaneously or submuscularly on the left side of patient 14 above the ribcage. Lead 20 may be implanted at least partially in a substernal space, such as at a target site between the ribcage or sternum 24 and heart 18. In one such configuration, a proximal portion of lead 20 may be configured to extend subcutaneously from IMD 12 toward sternum 24 and a distal portion of lead 20 may be configured to extend superior under or below sternum 24 in the anterior mediastinum 26 (FIG. 1C). Lead 20 may include one or more curved sections to configure lead 20 to naturally (e.g., in a self-biasing manner) extend in this way upon deployment. In some instances, the target site may substantially in the anterior mediastinum 26. The anterior mediastinum 26 is bounded laterally by the pleurae 28 (FIG. 1C), posteriorly by the pericardium 16 (FIG. 1C), and anteriorly by the sternum 24. In some instances, the anterior wall of the anterior mediastinum may also be formed by the transversus thoracics and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 20 extends along the posterior side of the sternum 24 substantially within the loose connective tissue or substernal musculature of the anterior mediastinum.

The term "substernal space" may refer to the region defined by the undersurface between sternum 24 and the body cavity but not including pericardium 16. In other words, the region is posterior to the sternum 24 and anterior to the ascending aorta. The substernal space may alternatively be referred to by the terms "retrosternal space" or "mediastinum" or "infrasternal" and may include the region referred to as the anterior mediastinum. Though the term substernal space is used throughout this disclosure for ease of description, it is to be understood that the term is interchangeable with any of the other aforementioned terms. Further, within this disclosure, the term "extra-pericardial" space may refer to a region around the outer heart surface but not within the pericardial sac or space. The region defined as the extra-pericardial space includes the gap, tissue, bone, or other anatomical features around the perimeter of, and adjacent to pericardium 16.

In other examples, lead 20 may be implanted at other extracardiovascular locations, such as being offset laterally to the left or the right of the sternum 24 or located over the sternum 24, or alternatively being configured to extend substantially parallel to the sternum 24 or be angled lateral from the sternum 24 at either the proximal or distal end upon implantation. Although described primarily in the context of an implantable medical device system including a lead having a distal portion located in the substernal space, other lead locations are contemplated. Lead 20 may be at least partially implanted in other intrathoracic locations, such as other non-vascular, extra-pericardial locations, including the gap, tissue, or other anatomical features around the perimeter of and adjacent to, but not attached to, pericardium 16 or other portion of heart 18 and not above the sternum 24 or ribcage.

Lead 20 may include an insulative lead body having a proximal end that includes connector 30 configured to be connected to IMD 12 and a distal portion that includes one or more electrodes. Lead 20 also includes one or more conductors that form an electrically conductive path within the lead body and interconnect the electrical connector and respective ones of the electrodes.

Lead 20 may include defibrillation electrodes 32A, 32B (individually or collectively "defibrillation electrode(s) 32"). In other examples, defibrillation electrodes 32A, 32B may functionally be different sections of a single defibrillation electrode 32, such that both defibrillation electrodes 32 are coupled to the same conductor or are otherwise configured to provide the same electrical stimulation. Though defibrillation electrodes 32 are depicted in FIGS. 1A-1C as coil electrodes for purposes of clarity, it is to be understood that defibrillation electrodes 32 may be of other configurations in other examples, such as an elongated coil electrode. Defibrillation electrodes 32 may be located on the distal portion of lead 20, where the distal portion of lead 20 is the portion of lead 20 that is configured to be implanted as extending along the sternum 24. Lead 20 may be implanted at a target site below or along sternum 24 such that a therapy vector between defibrillation electrodes 32 and a housing electrode formed by or on IMD 12 (or other second electrode of the therapy vector) is substantially across a ventricle of heart 18. The therapy vector may, in one example, be viewed as a line that extends from a point on defibrillation electrodes 32 (e.g., a center of one of the defibrillation electrodes 32) to a point on the housing electrode of IMD 12. As such, it may be advantageous to increase an amount of area across which defibrillation electrodes 32 (and therein the distal portion of lead 20) extends across heart 18. Accordingly, lead 20 may be configured to define a curving distal portion as depicted in FIG. 1A, which may enable lead 20 to provide relatively more efficacious pacing, sensing, and/or defibrillation to heart 18.

Based on the location of defibrillation electrodes 32 and the housing electrode of IMD 12 relative to heart 18, in some examples, one or more lungs (not shown in FIGS. 1A-1C) of patient 14 may be positioned at least partially in the path of the therapy vector used to deliver defibrillation shock(s) to heart 18 of patient 14. It has been determined that, in at least some examples, the position of the lung(s) of patient 18 when one or more defibrillation shocks is delivered may influence the DFT and/or therapeutic efficacy of the delivery defibrillation shocks. In some examples, depending on the position of the defibrillation electrodes on lead 20 and the position of IMD 14 relative to heart 18, the left lung volume may be more of interest than the right lung in term of influence of respiratory volume on defibrillation therapy. The cranial-caudal position of the heart relative to the electrodes and that syncs with diaphragm motion since the heart sits on top of the diaphragm may also be of interest.

As described herein, in some examples, the lung(s) of patient 14 may be positioned advantageously for the delivery of defibrillation shock(s) to heart 18 of patient 14 when the lung(s) are at a respiratory volume of at approximately end tidal or less. For example, a lower DFT and/or more therapeutically effective defibrillation therapy may result from the delivery of defibrillation shock(s) at a time when the lung(s) of patient 14 are at or near end tidal volume (e.g., by delivering the defibrillation shock(s) substantially coincidentally with the end of exhalation by patient 14. In this manner, a reduction in the amount of energy consumed by a device while still providing therapeutically effective defibrillation to patient 14 may result, which may allow a reduction in the size of a power source, reduced overall volume of IMD 12, and/or limiting the electroporation and/or troponin increase from delivery of defibrillation therapy. Electroporation and troponin release both may increase as shock energy increases. Electroporation and troponin release are associated with tissue damage from very high electric fields near the electrodes. These effects may be particularly evident near electrodes since, to get adequate field on the far side of the heart from the electrodes, the field strength at proximal tissue may be relatively higher and the proximal tissue may be overstimulated and can be damaged. Reducing the shock amplitude can reduce the extent of this damage or possibly eliminate it in some cases.

Lead 20 may also include one or more pace/sense electrodes 34A, 34B (individually or collectively, "pace/sense electrode(s) 34") located on the distal portion of lead 20. Electrodes 34 are referred to herein as pace/sense electrodes because they are generally configured for use in delivery of pacing pulses and/or sensing of cardiac electrical signals. In some instances, electrodes 34 may provide only pacing functionality, only sensing functionality, or both pacing functionality and sensing functionality. In the example illustrated in FIG. 1A and FIG. 1B, pace/sense electrodes 34 are separated from one another by defibrillation electrode 32B. In other examples, however, pace/sense electrodes 34 may be both distal of defibrillation electrode 32B or both proximal of defibrillation electrode 32B. In other examples, lead 20 may include more or fewer electrodes 32, 34 at various locations on lead 20. In some examples, IMD 12 may include one or more electrodes 32, 34 on another lead (not shown). Other lead configurations may be used, such as various electrode arrangements. For example, one or more pace/sense electrodes 34 may be placed between two defibrillation electrodes 32, such as described above. In an example, multiple pace/sense electrodes 34 may be placed between two defibrillation electrodes 32. In an example, two defibrillation electrodes 32 may be adjacent (e.g., such that the two defibrillation electrodes 32 are not separated by any pace/sense electrodes 34 between the two defibrillation electrodes 32). Other arrangements may additionally or alternatively be used.

Lead 20 may define different sizes and shapes as may be appropriate for different purposes (e.g., different patients or different therapies). As discussed above, in some examples, the distal portion of lead 20 may have one or more curved sections. As shown in the example of FIG. 1A, the distal portion of lead 20 is a serpentine shape that includes two "C" shaped curves, which together may resemble the Greek letter epsilon, "ε." Defibrillation electrodes 32 are each carried by one of the two respective C-shaped portions of the lead body distal portion. The two C-shaped curves extend or curve in the same direction away from a central axis of the lead body.

Pace/sense electrodes 34 may, in some instances, be approximately aligned with the central axis of the straight, proximal portion of lead 20. In this case, mid-points of defibrillation electrodes 32 are laterally offset from pace/sense electrodes 34. Other examples of extra-cardiovascular leads including one or more defibrillation electrodes and one or more pacing and sensing electrodes 34 carried by curving, serpentine, undulating or zig-zagging distal portion of the lead body 18 that may be implemented with the techniques described herein. In some examples, the distal portion of lead 20 may be straight (e.g., straight or nearly straight).

In some examples, system 10 may sense electrical signals, such as via one or more sensing vectors that include combinations of pace/sense electrodes 34 and/or a housing electrode of IMD 12. In some examples, IMD 12 may sense cardiac electrical signals using a sensing vector that includes one or both of the defibrillation electrodes 32 and/or one of defibrillation electrodes 32 and one of pace/sense electrodes 34 or a housing electrode of IMD 12. The sensed electrical intrinsic signals may include electrical signals generated by cardiac muscle and indicative of depolarizations and repolarizations of heart 18 at various times during the cardiac cycle. IMD 12 may be configured to analyze the electrical signals sensed by the one or more sensing vectors to detect tachyarrhythmia, such as ventricular tachycardia or ventricular fibrillation. In response to detecting the tachyarrhythmia, IMD 12 may begin to charge a storage element, such as a bank of one or more capacitors, and, when charged, deliver one or more defibrillation pulses via defibrillation electrodes 32 of lead 20 and/or the housing electrode if the tachyarrhythmia is still present. Additionally, or alternatively, IMD 12 may deliver pacing therapy via electrodes 32, 34 and/or the housing electrode of IMD 12. In some examples, the pacing therapy may include antitachycardia pacing (ATP).

System 10 may include external device 22. External device 22 may be a computing device that is configured for use in a home, ambulatory, clinic, or hospital setting to communicate with IMD 12 via wireless telemetry. Examples of communication techniques used by IMD 12 and external device 22 include radiofrequency (RF) telemetry, which may include an RF link established via Bluetooth, wireless local networks, or medical implant communication service (MICS). The communication may include one-way communication in which one device is configured to transmit communication messages and the other device is configured to receive those messages. Alternatively, or additionally, the communication may include two-way communication in which each device is configured to transmit and receive communication messages.

External device 22 may include communication circuitry configured to communicate per the techniques described above. External device 22 may be used to program commands or operating parameters of IMD 12 for controlling functioning of IMD 12 when configured external device 22 is configured as a programmer for IMD 12. External device 22 may be used to communicate with IMD 12 to retrieve data such as operational data, physiological data accumulated in IMD memory, or the like. As such, external device 22 may function as a programmer for IMD 12, an external monitor for IMD 12, or a consumer device such as a smartphone. External device 22 may be coupled to a remote patient monitoring system, such as CARELINK®, available from Medtronic plc, of Dublin, Ireland. A user may use external device 22 to program or update therapy parameters that define therapy or perform other activities with respect to IMD 12. The user may be a physician, technician, surgeon, electrophysiologist, or other healthcare professional. In some examples, the user may be patient 14.

Figure 2:
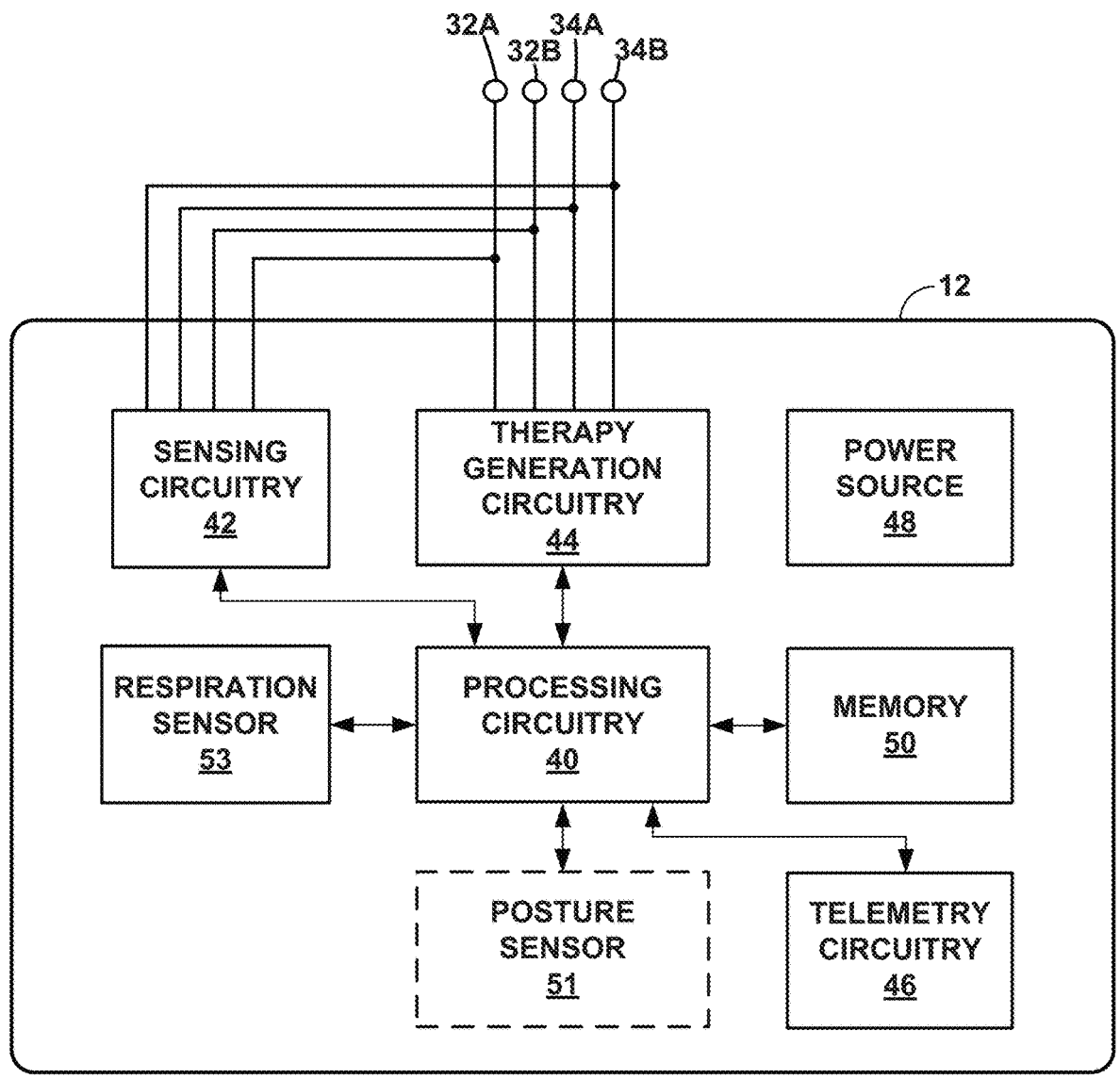
FIG. 2 is a functional block diagram of an example configuration of electronic components of an example IMD.

FIG. 2 is a functional block diagram of an example configuration of electronic components and other components of an example IMD 12. IMD 12 includes a processing circuitry 40, sensing circuitry 42, therapy generation circuitry 44, telemetry circuitry 46, power source 48, memory 50, posture sensor 51 and respiration sensor 53. The electronic components may receive power from a power source 48, which may be a rechargeable or non-rechargeable battery (e.g., a lithium-ion battery). In other embodiments, IMD 12 may include more or fewer electronic components. The described circuitry and other components may be implemented together on a common hardware component or separately as discrete but interoperable hardware or software components. Depiction of different features is intended to highlight different functional aspects and does not necessarily imply that such circuitry and other components must be realized by separate hardware or software components. Rather, functionality associated with one or more circuitries and components may be performed by separate hardware or software components, or integrated within common or separate hardware or software components.

Sensing circuitry 42 may be electrically coupled to some or all of electrodes 32 and 34 via the conductors of lead 20 and one or more electrical feedthroughs, or to the housing electrode via conductors internal to the housing of IMD 12. Sensing circuitry 42 is configured to obtain signals sensed via one or more combinations of electrodes 32 and 34 and the housing electrode of IMD 12 and process the obtained signals.

The components of sensing circuitry 42 may be analog components, digital components or a combination thereof. Sensing circuitry 42 may, for example, include one or more sense amplifiers, filters, rectifiers, threshold detectors, analog-to-digital converters (ADCs) or the like. Sensing circuitry 42 may convert the sensed signals to digital form and provide the digital signals to processing circuitry 40 for processing or analysis. For example, sensing circuitry 42 may amplify signals from the sensing electrodes and convert the amplified signals to multi-bit digital signals by an ADC. Sensing circuitry 42 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to processing circuitry 40.

In accordance with some examples of the disclosure, processing circuitry 40 may be configured to monitor the respiration (e.g., the cycling between of inhalation and exhalation) of one or both lungs of patient 14 to allow processing circuitry 40 to coordinate the delivery of one or more defibrillation shocks to heart 18 of patient 14 with the respiratory cycle of patient 14. Processing circuitry 40 may monitor the respiration of patient 14 using e.g., respiration sensor 53 and/or sensing circuitry 42. For example, sensing circuitry 42 and/or respiration sensor 53 may be employed such that processing circuitry 40 identifies one or more times at which the respiratory volume of a lung of a patient is at approximately end tidal volume or less, and IMD 12 may deliver one or more defibrillation shock(s) during the identified time at which the respiratory volume of a lung of a patient is at approximately end tidal volume or less. In some examples, IMD 12 may determine a time at which patient 14 is at or near the end of an exhale (e.g., at the end of an exhale, or just before or just after the end of an exhale) to identify a time at which the respiratory volume of a lung of a patient is at approximately end tidal volume or less. In some examples, processing circuitry 40 may not determine a value or otherwise measure the respiratory volume of the lungs of patient 14 but instead may determine the relative respiratory volume of the lungs, e.g., by distinguishing between period of inhalation and exhalation of patient 14, and delivering defibrillation therapy substantially coincidentally with approximately the end of an exhalation by patient 14.

Respiration sensor 53 may include one or more sensors configured to monitor the respiration of patient 14, such as a microphone configured to detect sounds associated with respiration of patient 14, a magnetometer configured to measure changes in dimensions of anatomical structures of the thorax of patient 14 during respiration, or a pressure sensor configured to measure changes in pressure exerted on lead 20 associated with changes in respiration. In some examples, an accelerometer may produce a signal that varies based on respiration, e.g., based on vibrations and/or movement associated with respiration. Sensing circuitry 42 may include filters, amplifiers, and/or analog-to-digital conversion circuitry, as examples, to condition any of these sensed signals for analysis by processing circuitry 40 and/or to detect features of the signals. In any such examples, processing circuitry 40 may determine a respiration state of patient 14 based on the signals obtained from electrodes 32, 34, and sensor 53, and may identify a time at which the respiratory volume of one or both lungs of patient 14 is at approximately end tidal volume or less. IMD 12 may then delivered one or more defibrillation shocks to heart 18 of patient 14 when the respiratory volume is at approximately end tidal volume or less.

In one example, IMD 12 may configured to sense and monitor the respiration of one or both lungs of patient 18, via sensing circuitry 42, by sensing impedance between two or more electrodes (e.g., two or more of pace/sense electrodes 34 and/or a housing electrode on housing 20. In some examples, respiration of one or both lungs of patient 18 may be monitored by using an impedance signal (e.g. transthoracic), where the respiratory signature is directly observable. For example, the impedance measured between the can electrodes and one or more of the electrodes 32, 34 is determined by the amount and type of tissue between the electrodes. Lung tissue impedivity decreases at end exhalation as non-conducting air is expelled. As a results, the impedance measured between the electrodes tends to decrease, e.g., to allow for the detection of the end of exhalation based on the monitored impedance.

Additionally, or alternatively, sensing circuitry 42 may configured to sense and monitor the respiration of one or both lungs of patient 18 by analyzing the cardiac EGM signal. For example, the EGM signal may have a lower frequency component resulting from changing in impedance associated with respiration that may otherwise be filtered out (e.g., with DC filter) of the EGM signal. The component may be analyzed to monitor the respiration of patient 14. In some examples, the EGM signal amplitude may vary with respiration as the heart moves relative to the electrodes.

Additionally, or alternatively, sensing circuitry 42 may configured to sense and monitor the respiration of one or both lungs of patient 18 by using respiration sensor 53 in the form of an accelerometer or an acoustic sensor (e.g., a microphone for sensing lung sounds). In some examples, respiration sensor 53 may be used to detect low amplitude respiratory tracing. The output of respiration sensor 53 in the form of an accelerometer may have a cyclic component created by motion of IMD 12 as the implant site tilts and moves with respiration of patient 14 which may be used to monitor respiration. A microphone or other acoustic sensor near the lungs may detect respiratory sounds in the same way that a stethoscope does. Processing of the that audio signal may extract that signal from interfering background noise to monitor the respiration of patient 14.

Additionally, or alternatively, sensing circuitry 42 may configured to sense and monitor the respiratory volume of one or both lungs of patient 18 with respiration sensor 53 in the form of a magnetometer and/or pressure sensor. A pressure sensor may be used, e.g., to evaluate pressure variability on lead 20 and/or the can of IMD 12 as an indicator of the respiration of patient 12. A magnetometer may be sensitive to motion within the earth's magnetic field and that would occur with respiration. A pressure sensor within the can of IMD 12 may be configured to respond to flexing of the can caused by respiration. A pressure sensor in the can may also have a variation caused by atmospheric pressure but that could be discarded with hi-pass filtering of the signal.

As shown in FIG. 2, IMD 14 may optionally include posture sensor 51. Posture sensor 51 allows IMD 12 to sense the posture occupied by patient 14. In such examples, IMD 14 may be configured to coordinate the delivery of one or more defibrillation shocks with the posture of patient 14, e.g., such that the defibrillation shocks are delivered when patient 14 occupies a particular posture (e.g., a lying posture or supine posture) in combination with the respiratory volume of one or more lungs of patient 14 being at approximately end tidal or less.

In the example of FIG. 2, posture sensor 51 may include one or more accelerometers, such as three-axis accelerometers, capable of detecting static orientation or vectors in three-dimensions (e.g., x, y, z coordinate vectors). Example accelerometers may include a micro-electro-mechanical systems (MEMS)-based accelerometer. In other examples, posture sensor 51 may alternatively or additionally include one or more gyroscopes, piezoelectric crystals, pressure transducers or other sensors to sense the posture of patient 12. Posture sensor data generated by posture sensor 51 and processing circuitry 40 may correspond to a posture occupied by patient 12, such as, a lying posture (e.g., including a supine (lying on back) posture), upright/standing posture, or reclined posture.

Although posture sensor 51 is described as containing the 3-axis accelerometer, posture sensor 51 may contain multiple single-axis accelerometers, dual-axis accelerometers, 3-axis accelerometers, or some combination thereof. In some examples, an accelerometer or other sensor may be located within or on IMD 12, on lead 20 (e.g., at the distal tip or at an intermediate position), an additional sensor lead positioned somewhere within patient 14, within an independent implantable sensor, or even worn on patient 14. For example, one or more microsensors may be implanted within patient 14 to communicate posture information wirelessly to IMD 12. In this manner, the patient posture may be determined from multiple posture sensors placed at various locations on or within the body of patient 14.

In one example, each of the x, y, and z signals provided by the posture sensor has both a DC component and an AC component. The DC components describes the gravitational force exerted upon the sensor and can thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient, assuming proper orientation of the sensor to the patient's body.

Example systems and techniques for detecting the posture of patient 14 using posture sensor 51 may include one or more of the examples described in U.S. Pat. No. 8,708,934 to Skelton et al., the entire content of which is incorporated herein by reference.

In the illustrated example of FIG. 2, sensing circuitry 42 and posture sensor 51 are both enclosed within the housing of IMD 12. In other examples, all or a portion of one or both of sensing circuitry 42 and posture sensor 51 may be located on a lead that is coupled to IMD 12 or may be implemented in a remote sensor that wirelessly communicates with IMD 12. In any case sensing circuitry 42 and posture sensor 51 are electrically or wirelessly coupled to circuitry contained within IMD 12.

Processing circuitry 40 may process the signals from sensing circuitry 42 to monitor electrical activity of heart 18 of patient 14. Processing circuitry 40 may store signals obtained by sensing circuitry 42 as well as any generated EGM waveforms, marker channel data or other data derived based on the sensed signals in memory 50. Processing circuitry 40 may analyze the EGM waveforms and/or marker channel data to detect cardiac events (e.g., tachycardia). In response to detecting the cardiac event, processing circuitry 40 may control therapy generation circuitry 44 to deliver the desired therapy to treat the cardiac event, e.g., defibrillation shock, cardioversion shock, ATP, post shock pacing, or bradycardia pacing.

Therapy generation circuitry 44 is configured to generate and deliver electrical stimulation therapy to heart 18. Therapy generation circuitry 44 may include one or more pulse generators, capacitors, and/or other components capable of generating and/or storing energy to deliver as pacing therapy, defibrillation therapy, cardioversion therapy, cardiac resynchronization therapy, other therapy or a combination of therapies. In some instances, therapy generation circuitry 44 may include a first set of components configured to provide pacing therapy and a second set of components configured to provide defibrillation therapy. In other instances, therapy generation circuitry 44 may utilize the same set of components to provide both pacing and defibrillation therapy. In still other instances, therapy generation circuitry 44 may share some of the defibrillation and pacing therapy components while using other components solely for defibrillation or pacing.

Processing circuitry 40 may control therapy generation circuitry 44 to deliver the generated therapy to heart 18 via one or more combinations of electrodes 32 and 34 and the housing electrode of IMD 12 according to one or more therapy programs, which may be stored in memory 50. Processing circuitry 40 controls therapy generation circuitry 44 to generate electrical stimulation therapy with the amplitudes, pulse widths, timing, frequencies, electrode combinations or electrode configurations specified by a selected therapy program.

In the case of pacing therapy, e.g., ATP, post-shock pacing, and/or bradycardia pacing provided via one or more of electrodes 34 of lead 20, processing circuitry 40 controls therapy generation circuitry 44 may generate and deliver pacing pulses with any of a number of shapes, amplitudes, pulse widths, or other characteristic to capture heart 18. For example, the pacing pulses may be monophasic, biphasic, or multi-phasic (e.g., more than two phases). The pacing thresholds of heart 18 when delivering pacing pulses from the substernal space, e.g., from electrode(s) 34 substantially within anterior mediastinum 26, may depend upon a number of factors, including location, type, size, orientation, and/or spacing of electrodes 28 and 30, location of IMD 12 relative to electrodes 34, physical abnormalities of heart 18 (e.g., pericardial adhesions or myocardial infarctions), or other factor(s).

In the case of cardioversion or defibrillation therapy, e.g., cardioversion or defibrillation shocks provided by one or more of defibrillation electrode 32A and 32B of lead 20, processing circuitry 40 controls therapy generation circuitry 44 to generate cardioversion or defibrillation shocks having any of a number of waveform properties, including leading-edge voltage, tilt, delivered energy, pulse phases, and the like. Therapy generation circuitry 44 may, for instance, generate monophasic, biphasic or multiphasic waveforms. Additionally, therapy generation circuitry 44 may generate cardioversion or defibrillation waveforms having different amounts of energy. As with pacing, delivering cardioversion or defibrillation shocks from the substernal space, e.g., from electrode(s) 32 substantially within anterior mediastinum 26, may reduce the amount of energy that needs to be delivered to defibrillate heart 18. As one example, therapy generation circuitry 44 may generate and deliver cardioversion or defibrillation shocks having energies of less than 80 Joules (J). As another example, therapy generation circuitry 44 may generate and deliver cardioversion or defibrillation shocks having energies of less than 65 J. As one example, therapy generation circuitry 44 may generate and deliver cardioversion or defibrillation shocks having energies of less than 60 J. In some instances, therapy generation circuitry 44 may generate and deliver cardioversion or defibrillation shocks having energies of about 40 to about 50 J (e.g., about 40 J). In other instances, therapy generation circuitry 44 may generate and deliver cardioversion or defibrillation shocks having energies of about 35 to about 60 J. In still other instances, therapy generation circuitry 44 may generate and deliver cardioversion or defibrillation shocks having energies less than 35 J. Subcutaneous IMD systems on the other hand generate and deliver cardioversion or defibrillation shocks having an energy around 80 J. Placing defibrillation lead 20 within the substernal space, e.g., with the distal portion substantially within anterior mediastinum 26, may result in reduced energy consumption and, in turn, smaller devices and/or devices having increased longevity.

As described herein, in some examples, therapy system 10, e.g., processing circuitry 40, may be configured to time the delivery of defibrillation therapy (e.g., one or more defibrillation shocks) such that the electrical stimulation shock(s) (pulse(s)) are delivered to heart 18 of patient 14 when the respiratory volume of the lung(s) of patient 14 are at approximately end tidal volume or less. For example, therapy system 10 may be configured to identify a time at which a respiratory volume of a lung of patient 18 (e.g., the left lung of patient 14) is at approximately end tidal volume or less, e.g., by monitoring the respiratory cycle of patient 18 using sensing circuitry 42, and then deliver one or more defibrillation shocks to heart 18 using electrode(s) 32 and the housing electrode of IMD 12 when the respiratory volume of the lung of a patient is at the approximately end tidal volume or less. As described herein, in some example, controlling the delivery of one or more defibrillation shocks to coincide with, e.g., the approximately end of an exhalation by a patient or at another time in which the respiratory volume of patient 14 is at approximately end tidal or less, may provide for a lower DFT and/or more effective defibrillation shock, e.g., compared to delivery of one or more defibrillation shocks when the respiratory volume of patient 14 is greater than at approximately end tidal at or near the end of the inhalation by the patient.

Therapy generation circuitry 44 may also generate defibrillation waveforms having different tilts. In the case of a biphasic defibrillation waveform, therapy generation circuitry 44 may use a 65/65 tilt, a 50/50 tilt, or other combinations of tilt. The tilts on each phase of the biphasic or multiphasic waveforms may be the same in some instances, e.g., 65/65 tilt. However, in other instances, the tilts on each phase of the biphasic or multiphasic waveforms may be different, e.g., 65 tilt on the first phase and 55 tilt on the second phase. The example delivered energies, leading-edge voltages, phases, tilts, and the like are provided for example purposes only and should not be considered as limiting of the types of waveform properties that may be utilized to provide substernal defibrillation via defibrillation electrode 24.

Telemetry circuitry 46 includes any suitable hardware, firmware, software or any combination thereof for communicating with another device, such as a clinician programmer, a patient monitoring device, or the like. For example, telemetry circuitry 46 may include appropriate modulation, demodulation, frequency conversion, filtering, and amplifier components for transmission and reception of data with the aid of an antenna, which may be located within connector block of IMD 12 or within housing IMD 12.

The various components of IMD 12 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Processing circuitry 40 may include fixed function circuitry and/or programmable processing circuitry. The functions attributed to processing circuitry 40 herein may be embodied as software, firmware, hardware or any combination thereof.

Memory 50 may include computer-readable instructions that, when executed by processing circuitry 40 or other component of IMD 12, cause one or more components of IMD 12 to perform various functions attributed to those components in this disclosure. Memory 50 may include any volatile, non-volatile, magnetic, optical, or electrical media, such as a random-access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

Figure 3:
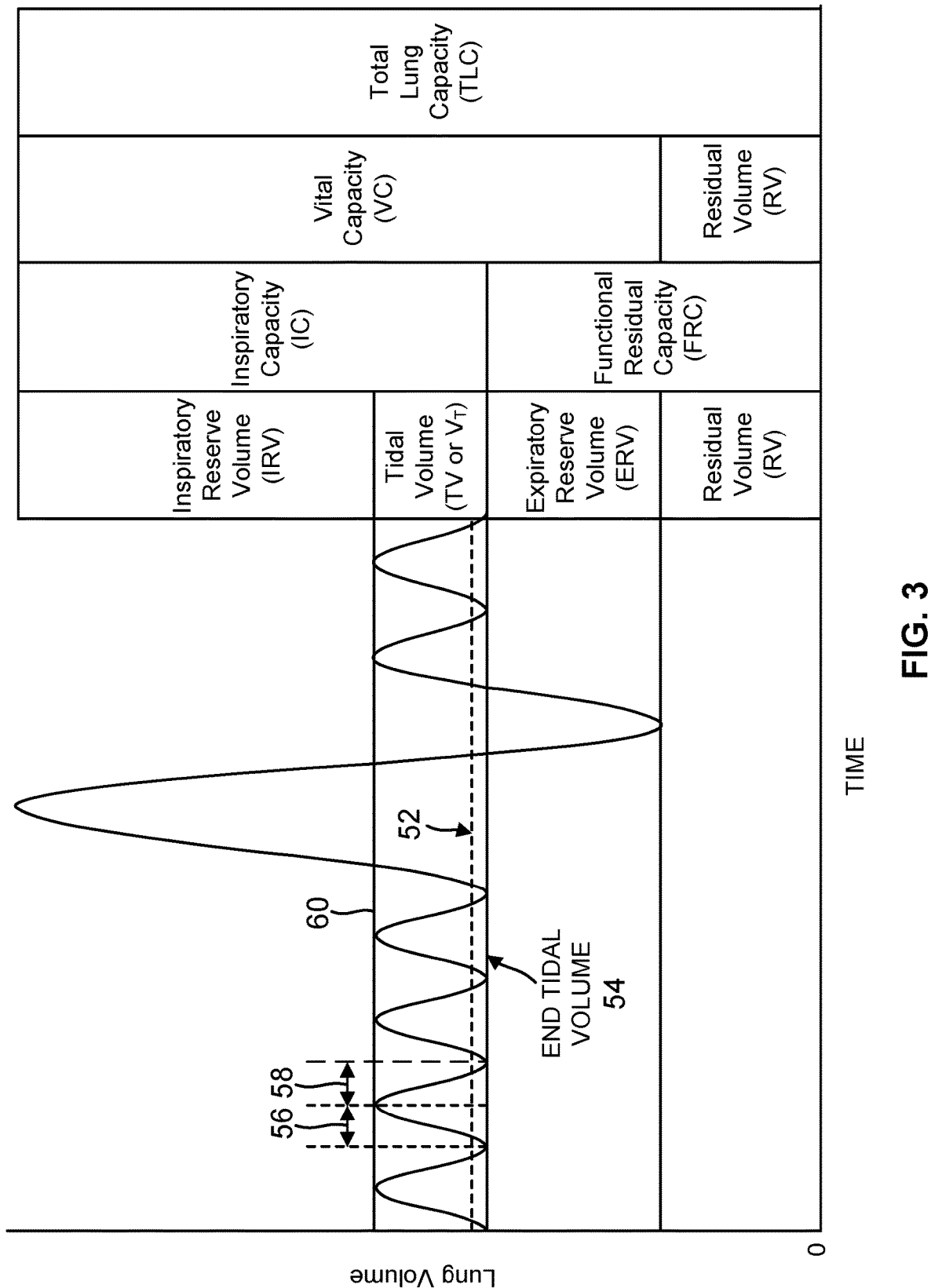
FIG. 3 is a conceptual diagram illustrating the respiratory volume of the lungs at various stages.

FIG. 3 is a conceptual diagram illustrating the various components of respiratory volume of the lungs of a patient, such as patient 14, over an example period of time. The respiratory volume for a lung may be the amount of air contained within the lung at a given time. The respiratory volume may be dependent on the amount of air inhaled (e.g., during normal resting inhalation 56), exhaled (during normal resting exhalation 58), and stored within the lungs at a given time.

As shown in FIG. 3, a respiration cycle for patient 14 may include a period of inhalation 56 followed by a period of exhalation 58 such that the respiratory volume of the lung(s) cycle between the maximum tidal volume 60 following the inhalation period 56 and end tidal volume 54 following the exhalation period 58. During inhalation 56, the diaphragm may contract and pull downward while the muscles between the ribs contract and pull upward. This increases the size of the thoracic cavity and decreases the pressure inside. As a result, air rushes in and fills the lungs. During exhalation 58, the diaphragm relaxes, and the volume of the thoracic cavity decreases, while the pressure within it increases. As a result, the lungs contract and air is forced out.

As illustrated in FIG. 3, tidal volume may refer to the amount of air which enters the lungs during normal inhalation when a patient is at rest, e.g., as opposed to exercising. For example, if patient 14 is sitting normally and breathing quietly then the total amount of air breathed in during the inhalation may be the tidal volume. The amount of air within the lungs following normal exhalation may be referred to as end tidal volume 54. An example tidal volume for patient 14 may be approximately 500 milliliters. Inspiratory reserve volume may refer to the amount of extra air that may be inhaled above tidal volume during a deep breath. For example, if patient 14 is breathing in a normal amount while at rest, the maximum additional air beyond the normal tidal inspiration that patient 14 may breath in constitutes the inspiratory reserve volume. Conversely, expiratory reserve volume may refer to the amount of extra air exhaled, beyond tidal volume, during a forceful breath. For example, if patient 14 were to breathe out normally, and then try and breathe out even more until he/she physically cannot breathe out any more air, that amount exhaled after end tidal volume 54 constitutes the expiratory reserve volume. Residual volume may refer to the amount of air left in the lungs following maximum exhalation. This amount prevents the lungs of patient 14 from collapsing. Vital capacity may refer to the maximum amount of air one can exhale after taking the deepest breath possible. Total lung capacity may refer to the vital lung capacity plus the residual volume and is the total amount of air the lungs can hold.

In accordance with examples of the disclosure, a medical device system such as system 10 of FIG. 1 may be configured to coordinate delivery of defibrillation shock(s) to a patient when the lung(s) of the patient are at approximately end tidal volume or less. An example of such respiratory volume is represented by threshold 52 shown in FIG. 3, wherein threshold 52 corresponds to approximately end tidal volume. Medical device system 10 may be configured to deliver defibrillation shock(s) to heart 18 of patient 14 (e.g., when VF or VT of heart 18 is detected) at a point in time when respiratory volume of patient 14 is at threshold 52 or less. As described herein, IMD 12 may be configured to determine a time at which the respiratory volume of one or more lungs of patient 14 is at approximately end tidal volume or less, e.g., by monitoring the respiration (inhalation and/or exhalation) of patient 14.

In some examples, threshold 52 may be equal to the end tidal volume 54 of patient 14. In some examples, threshold 52 may be about 50%, about 40% about 35%, about 30%, about 25%, about 20%, about 15%, about 10%, about 5%, about 2.5% of the tidal volume of patient 18. In other examples, from a temporal standpoint, threshold 52 may represent the respiratory volume of the lung(s) of patient 14 about 5 seconds, about 4 seconds, about 3 seconds, about 2 seconds or about 1 second before and/or after the occurrence of the end tidal volume 54 of the lung(s) of patient 14. In some examples, threshold 52 may set as an absolute value of lung volume above the end tidal volume of the lung(s) of patient 14. In some examples, threshold 52 may be the respiratory volume of the lung(s) of patient 14 about 5 seconds, about 3 seconds, or about 2 second or about 1 second after the start of an exhalation period of patient 14 and/or about 5 seconds, about 3 seconds, about 2 seconds or about 1 second after the start of an inhalation period of patient 12.

In other examples, rather than deliver the defibrillation shock at or near end tidal exhalation, a particular patient could receive defibrillation shock(s) that are timed to be anywhere within the cardiac cycle at the clinician's discretion. The factors determining the timing may be the relative alignment of the electrodes, heart and can, and/or lung volume.

Figure 4:
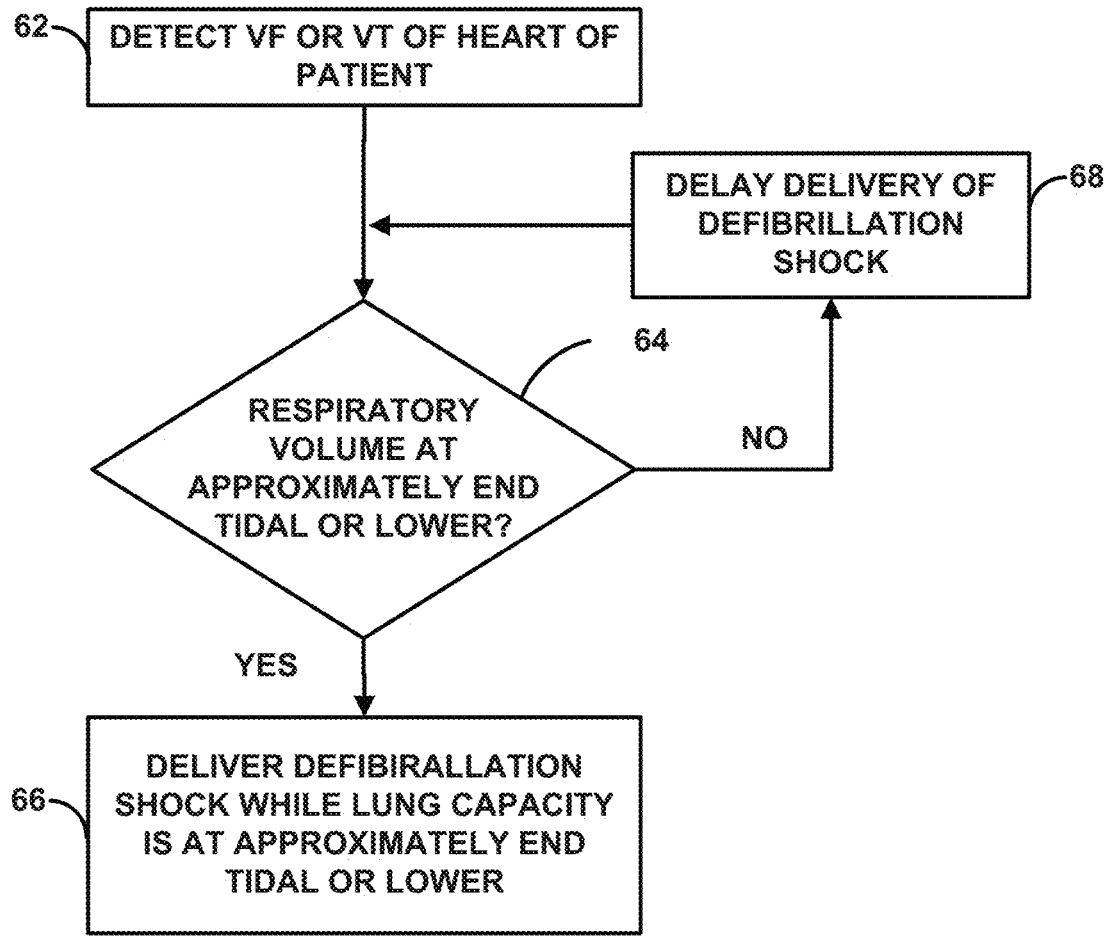
FIG. 4 is a flow diagram illustrating an example technique for coordinating the delivery of defibrillation shock(s) with the respiration of a patient.

FIG. 4 is a flow diagram illustrating an example technique in accordance with some examples of the disclosure. The example technique of FIG. 4 is described as being carried out by medical device system 10 of FIG. 1 on patient 14 for ease of description. However, any suitable medical device system may employ the example technique to deliver defibrillation stimulation therapy to a patient, including any suitable extravascular ICD system.

As shown in FIG. 4, processing circuitry 40 of IMD 14 may determine that heart 18 of patient 14 is in the state of VF or VT, or otherwise in the need of defibrillation stimulation therapy (62). Processing circuitry 40 may make such a determination using any suitable technique. For example, processing circuitry 40 may sense electrical activity of heart 18 using sensing circuitry 42 to detect the occurrence of VF or VT, or other electrical activity that indicates that defibrillation therapy should be delivered to defibrillate the heart 18 of patient 14. While in the example of FIG. 4, IMD 12 determines that patient 14 needs defibrillation stimulation therapy upon detecting VT or VF of heart 18, other scenarios in which heart 18 of patient 14 is in need of defibrillation stimulation therapy are contemplated.

In response to the detection of VF or VT of heart 18 (62), processing circuitry 40 of IMD 12 determines whether or not the respiratory volume of one or more lungs (e.g., the left lung or both right and left lung) of patient 18 is at approximately end tidal volume or less (64). Any suitable technique may be employed by IMD 12 that allows for the identification of a time when the respiratory volume of one or both lungs of patient 14 is at approximately end tidal or less. For example, as described above, processing circuitry 40 may monitor the respiratory volume of one or more lungs of patient 14 using sensing circuitry 42 and/or respiration sensor 53. In some examples, to identify a time when the respiratory volume of one or both lungs of patient 14 is at approximately end tidal volume or less, processing circuitry 40 may monitor the respiratory cycle of patient 14 to determine when patient 14 is at or near the end of an exhalation phase of the respiratory cycle. The time that patient 14 is at or near at or near the end of an exhalation phase of the respiratory cycle may correspond to a time when the lung(s) of patient 14 are at approximately end tidal volume or less. Conversely, processing circuitry 40 may determine that the respiratory volume of patient 14 is not at approximately end tidal volume or less by determining that patient is at or near the end of an inhalation phase of the respiratory cycle.

If processing circuitry 40 determines that the respiratory volume is at approximately end tidal or less (64), processing circuitry 40 may control therapy generation circuitry 44 to deliver one or more defibrillation shocks to heart 18 of patient 14 via one or more of electrodes 32 on lead 20 when the respiratory volume of one or more lungs of patient 14 is at approximately end tidal volume or less (66). The one or defibrillation shocks may be configured to defibrillate heart 18 by delivering an amount of energy sufficient to end the dysrhythmia of heart 18. The amount of energy of the delivered defibrillations shock(s) may be at or above the defibrillation threshold (also referred to as DFT) for heart 18 of patient 14.

In some examples, processing circuitry 40 determines that the respiratory volume is at approximately end tidal or less when patient 14 is determined to be at or near an end of exhalation, e.g., using respiration sensor 53. In some examples, processing circuitry 40 may time the delivery of one or more defibrillation shocks to be within a set amount of time of the end of exhalation by patient 14. For example, processing circuitry 40 may identify an approximately end of exhalation via respiration sensor 53 and control therapy generation circuitry 44 to deliver the defibrillation shock(s) within about 5 second, about 2.5 seconds, or about 1 second within (i.e., before or after) the end of patient 14 exhalation (e.g., where the respiratory volume is about 50% or less of the tidal volume at the time the shock(s) are delivered). In some example, processing circuitry 40 may delivery the defibrillation shock at the end of exhalation or within about 25% of the overall respiration cycle (e.g., in terms of time) before or after the end of exhalation.

In some example, processing circuitry 40 may identify an approximate end of inhalation by patient 14 via respiration sensor 53 and then deliver defibrillation shock(s) to patient 14 a set amount of time following the approximately end of inhalation so that the defibrillation shocks may substantially coincide with the respiratory volume of patient 14 being at approximately end tidal volume or less. For example, processing circuitry 40 may identify an approximately end of inhalation via respiration sensor 53 and control therapy generation circuitry 44 to deliver the defibrillation shock(s) after about 1 second, after about 2 seconds, after about 5 seconds, after about 7 seconds, or after about 10 seconds of the end of patient 14 inhalation (e.g., where the shock is delivered at about 50% or less of tidal volume following the end of inhalation). In some example, timing from end inhalation to identify end exhalation may be sensitive to respiratory rate and this might be affected by VT or VF of patient 14. Processing circuitry 40 may be configured to compensate by sensing the cyclic signal and dividing by about two to estimate end exhalation of patient 14. Processing circuitry 40 may time the delivery of defibrillation shock(s) off the inhalation of patient 14 to delay by one half of the cycle (+/−one quarter cycle).

Conversely, if processing circuitry 40 determines that the respiratory volume is not at approximately end tidal or less (64), processing circuitry 40 may control therapy generation circuitry 44 to withhold or otherwise delay the delivery of the one or more defibrillation shocks (68). During the delay in the delivery of the one or more defibrillation shocks (68), processing circuitry 40 may continue to evaluate the respiratory volume of the lung(s) of patient 14 (e.g., via sensing circuitry 42) to identify a time when the lung(s) of patient 14 transition to a respiratory volume that is approximately end tidal or less. In response to subsequently determining that the respiratory volume that is approximately end tidal or less, processing circuitry 40 may then control therapy generation circuitry 44 to deliver one or more defibrillation shocks to heart 18 of patient 14 via one or more of electrodes 32 on lead 20 when the respiratory volume of one or more lungs of patient 14 is at approximately end tidal volume or less (66).

Although not shown in FIG. 4, in some examples, processing circuitry 40 may be unable to determine the respiratory volume of the lung(s) of patient 14 following the detection of VF or VT of heart 18 of patient 14 (62), e.g., due to an error in sensing circuitry 42. In such an instance, processing circuitry 40 may be configured to identify that the respiratory volume of patient 14 is undetermined and control therapy generation circuitry to deliver one or more defibrillation shocks to heart 18 of patient 14 without coordinating the defibrillation shock(s) to coincide with the respiratory volume of the lung(s) being at approximately end tidal volume or less.

Figure 5:
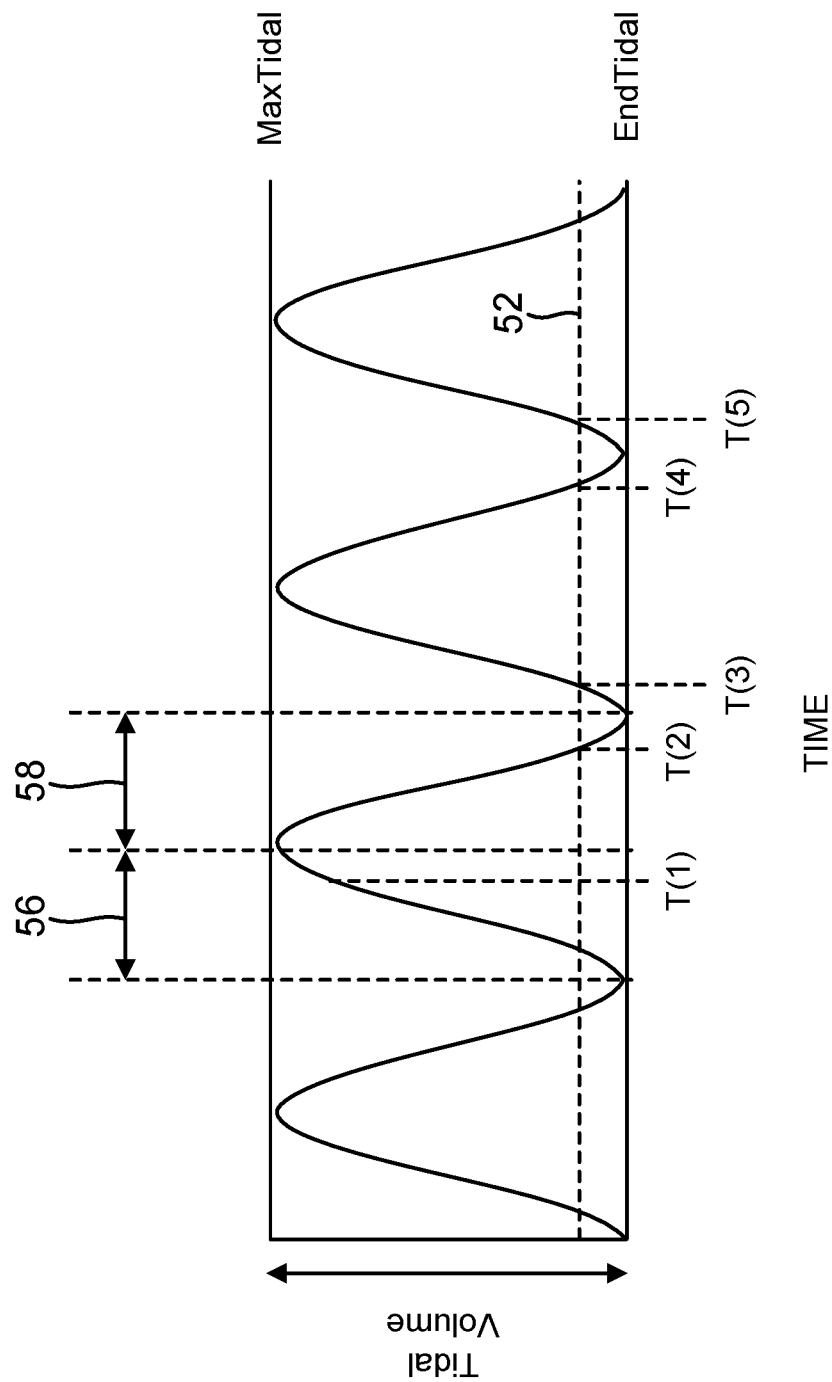
FIG. 5 is a conceptual diagram illustrating the timing of the delivery of a defibrillation shock in coordination with the respiration of a patient, e.g., in accordance with the example technique of FIG. 4.

FIG. 5 is a conceptual diagram illustrating example timing of various steps of the example technique of FIG. 4 with regard to the respiratory volume of the lung(s) of patient 14. For example, processing circuitry 40 may detect the VF or VT of heart 18 of patient 14 (62) at time T(1) which occurs during inhalation 56 by patient 14. Rather than processing circuitry 40 automatically controlling therapy generation circuitry 44 to deliver one or more defibrillation shocks to substantially coincide with the detection of VF or VT of the heart 18 of patient, processing circuitry 40 may, e.g., evaluate the respiratory volume of patient 18 in response to the detection of VF or VT of heart 18.

As shown in FIG. 5, the respiratory volume of the lung(s) of patient 14 may not be at approximately end tidal volume (represented by threshold 52) until after patient 14 completes the inhalation 56 by patient 14 that coincides with processor's 40 detection of the VF or VT of heart 18 of patient 14 as well as at least an initial portion of the subsequent exhale by patient 14. In accordance with the technique of FIG. 4, processing circuitry 40 may delay or otherwise withhold the deliver of defibrillation shock(s) until after patient 14 completes the inhalation 56 by patient 14 that coincides with processing circuitry's 40 detection of the VF or VT and after at least the initial portion of the subsequent exhalation. In such a scenario, therapy generation circuitry 44, under the control of processing circuitry 40, may not deliver the one or more defibrillation shocks to patient 14 until time T(2) but not after time T(3), i.e., IMD 12 delivers the one or more defibrillation shocks to patient 14 at or during a time when the respiratory volume of the lung(s) of patient 14 is at or below threshold 52. As described herein, threshold 52 represents a respiratory volume of the lung(s) of patient 14 being approximately end tidal volume of less.

Additionally or alternatively, processing circuitry 40 may control therapy generation circuitry 44 to deliver defibrillation shock(s) from time T(4) to T(5). For example, rather than IMD 14 delivering defibrillation shock(s) to patient 14 the first instance of the respiratory volume being at or below threshold 52 following the detection of VF or VT detection, IMD 14 may not deliver defibrillation pulses the first instance of lung(s) of patient 14 being below threshold 52 but may delay delivery of defibrillation shock(s) until the next or an otherwise subsequent occurrence of the respiratory volume of patient 14 being at or below threshold 52.

In some examples, a defibrillation shock may be delivered at some point from T(2) to T(3) and T(4) to T(5), e.g., when the shock delivered from T(2) to T(3) was not successful in defibrillating heart 18. In some examples, a defibrillation shock may be delivered without regard to the respiration of patient 14, e.g., after one or more defibrillation shocks coordinated with the respiration of patient 14 is not successful. In some examples, a defibrillation shock may be delivered at some point from T(2) to T(3) and then again at some point from T(3) to T(4).

While the detection of VF or VT of heart 18 is shown in FIG. 5 as occurring during inhalation 56 by patient 14, other examples may include the detection of VF or VT of heart 18 during exhalation by patient 14. In such a scenario, IMD 12 may still withhold or otherwise delay the delivery of defibrillation shocks if the respiratory volume of the lung(s) of patient 14 is above threshold 52 when the VF or VT is detected. In instances in which the VT or VF of heart 18 is detected at a time during which the respiratory volume of lung(s) of patient 14 is at or below threshold 52, IMD 12 may deliver the defibrillation shock(s) before the respiratory volume of the lung(s) rises above threshold 52 (e.g., the defibrillation shock(s) may be delivered approximately coincidentally with the detection of the VF or VT of heart 18 by IMD 12). Put another way, if IMD 12 detects a VF or VT of heart 18 from time T(2) to T(3), IMD 12 may deliver one or more defibrillation shock(s) to heart 18 of patient 14 at or before T(3). Additionally or alternatively, if IMD 12 detects a VF or VT of heart 18 from time T(2) to T(3), IMD 12 may wait to deliver one or more defibrillation shocks until some point from time T(4) to T(5) or other subsequent occurrence of the respiratory volume of patient 14 being at approximately end tidal volume or less.

IMD 12 may monitor the respiration of patient 12 continuously or periodically, e.g., to carry out the technique of FIG. 4. In some examples, processing circuitry 40 continuously monitor the respiratory cycle of patient 14, e.g., in combination with monitoring for VT or VF of heart 18 of patient 14, to continuously identify time(s) at which the respiratory volume of patient 14 is at approximately end tidal volume or less. Data indicative of the monitored respiration of patient 14 may be stored by processing circuitry, e.g., in memory 50. Upon detecting the VT or VF of heart 18, processing circuitry 40 may access the respiration data stored in memory 50 in response to the detection to determine if the respiratory volume of patient 14 is at approximately end tidal volume or less (e.g., if patient is at or near the end of an exhalation. As described above, IMD 12 may deliver defibrillation shock(s) to heart 18 of patient 14 if the respiratory volume is at approximately end tidal volume or less or delay the delivery of the defibrillation shock(s) if the respiratory volume is not at approximately end tidal volume or less. In other examples, processing circuitry 40 may initiate the monitoring of the respiration of patient 14 based on the detection of VT or VF of patient. For example, upon detecting VF or VT of heart 14, IMD 12 may then initiate monitoring the respiration of patient 14 to identify a time at which the respiratory volume of patient 14 is at approximately end tidal volume or less.

Figure 6:
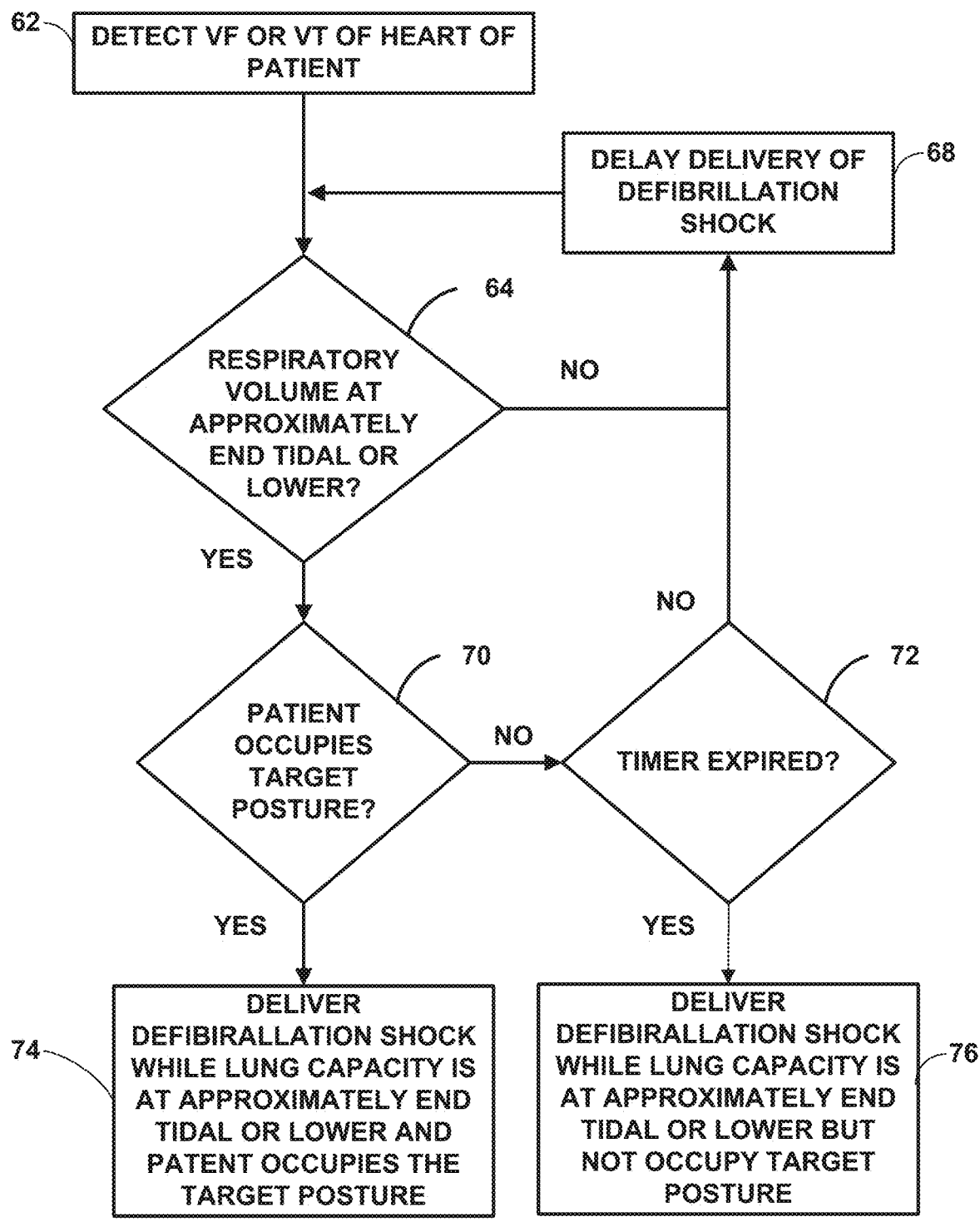
FIG. 6 is a flow diagram illustrating an example technique for coordinating the delivery of defibrillation shock(s) with the respiration of a patient and the posture of the patient.

FIG. 6 is a flow diagram illustrating another example technique for coordinating the delivery of defibrillation pulses with the respiration of a patient. The example technique of FIG. 6 is similar to that of the example technique of FIG. 4, and similar steps are similarly numbered. Additionally, the example technique of FIG. is described as being carried out by medical device system 10 of FIG. 1 on patient 14 for ease of description. However, any suitable medical device system may employ the example technique to deliver defibrillation stimulation therapy to a patient, including any suitable extravascular ICD system.

In addition to timing the delivery of defibrillation pulses to coincide with the respiratory volume of a patient's lung(s) being approximately end tidal volume or below, e.g., as described in the technique of FIG. 4, the example technique of FIG. 6 also coordinates the delivery of the defibrillation pulses with the posture of a patient. As such, the technique of FIG. 6 may include the delivery of defibrillation shock(s) to a patient such that the delivery coincides with the respiratory volume of patient 14 being at approximately end tidal or less and while patient 14 occupies a target posture. In cases in which the processing circuitry 40 detects a VF or VT of heart 18 at a time when patient 14 is not in a target posture and/or does not have a respiratory volume of approximately end tidal or less, then processing circuitry 40 may delay the delivery of defibrillation shock(s) to the heart 18 of patient 14 until both conditions are met.

As shown in FIG. 6, processing circuitry 40 of IMD 14 may determine that heart 18 of patient 14 is in the state of VF or VT, or otherwise in the need of defibrillation therapy (62). In response, processing circuitry 40 may identify whether or not the respiratory volume of one or more lungs of patient 14 is at approximately end tidal or lower (e.g., by detecting whether or not patient 14 is at approximately at end of exhalation) (64). If processing circuitry 40 determines that the respiratory volume is not at approximately end tidal or less (64), processing circuitry 40 may control therapy generation circuitry 44 to withhold or otherwise delay the delivery of the one or more defibrillation shocks (68).

Conversely, if processing circuitry 40 determines that the respiratory volume is at approximately end tidal or less (64), processing circuitry 40 may determine, via posture sensor 51, whether or not patient 14 occupies a target posture (70). If processing circuitry 40 determines that patient 14 does occupy the target posture (70) in addition to the respiratory volume of patient 14 being at approximately end tidal or less, then processing circuitry 40 may control therapy generation circuitry 44 to deliver one or more defibrillation shocks to heart 18 of patient 14 via one or more of electrodes 32 on lead 20 when the respiratory volume of one or more lungs of patient 14 is at approximately end tidal volume or less and patient occupies the target posture (74). The one or defibrillation shocks may be configured to defibrillate heart 18 by delivering an amount of energy sufficient to end the dysrhythmia of heart 18. The amount of energy of the delivered defibrillations shock(s) may be at or above the defibrillation threshold (also referred to as DFT) for heart 18 of patient 14.

However, if processing circuitry 40 determines that patient 14 does not occupy the target posture (70), then processing circuitry 40 may again control therapy generation circuitry 44 to withhold or otherwise delay the delivery of the one or more defibrillation shocks (68). As shown in FIG. 6, this delay in delivery of defibrillation shock(s) to the heart 18 of patient 14 may be subject to the expiration of a timer (72). If processing circuitry 40 determines that patient 14 does not occupy the target posture but that the timer has expired, then processing circuitry 40 may control therapy generation circuitry 44 to deliver one or more defibrillation shocks to heart 18 of patient 14 via one or more of electrodes 32 on lead 20 when the respiratory volume of one or more lungs of patient 14 is at approximately end tidal volume or less but patient 14 does not occupy the target posture. The timer may correspond to an amount of time for which it is appropriate to delay the delivery of defibrillation shock(s) to patient 14 following detection of VT or VF of heart 18 of patient 14 without unnecessary influencing the effectiveness of the therapy regardless of the DFT level. The timer may be utilized based on the recognition that patient 14 may not occupy the target posture within a reasonable amount of time following the detection of VF or VT of heart 18, e.g., if patient is in a reclined or sitting posture then he/she may not transition to a lying posture such as a supine posture within a reasonable amount of time. The timer may start upon detecting VF or VT and may be a pre-programmed value set, e.g., by a clinician during a programming session. In some examples, the timer may expire after, e.g., about 5 second, about 10 seconds, about 15 seconds, about 20 second, about 30 seconds, or about 45 seconds although other values are contemplated. In some cases, the length of the timer may be set by a clinician with a default value that is supplied by the manufacturer of the implantable medical device system.

Although not shown in FIG. 3, in some examples, a timer similar to that described for the example technique of FIG. 6 may be used so that the delivery of a defibrillation shock may not be delayed too long, e.g., in cases in which IMD 12 is not able to identify respiration of patient 14 following the detection of VT or VT of patient 14. In such cases, the timer may expire after, e.g., about 5 second, about 10 seconds, about 15 seconds, about 20 second, about 30 seconds, or about 45 seconds although other values are contemplated.

The target posture of patient 14 may correspond to a posture in which it may be desirable to deliver defibrillation shock(s) to patient 14 while the patient occupies the posture at the same time in which the respiratory volume of patient 14 is at approximately end tidal or less. For example, the combination of the respiratory volume of patient 14 being approximately end tidal or less and the patient occupying the target posture may provide for a lower DFT and/or more effective defibrillation shock, e.g., compared to delivery of one or more defibrillation shocks when the respiratory volume of patient 14 is at approximately end tidal or less but when patient does not occupy the target posture. As one example, a lower DFT for a supine posture may be realized versus an upright posture, and occupying a supine posture in addition to patient 14 be at approximately at the end of an exhale may result in an even better (e.g., lower) DFT than patient 14 being in a supine posture while at or near the end of an inhale. In accordance with the example technique of FIG. 6, a medical device system with the ability to monitor patient posture at the time of defibrillation, along with respiration, may allow for the tailored defibrillation treatment strategy.

The target posture may be a pre-programmed value (e.g., defined by a clinician during a programming session) determined on a patient-by-patient basis or may be a predefined value that is set for all patients. In some examples, the target posture may be a supine posture or other lying posture (e.g., lying left, lying right, lying front) and may be a single posture or a set of multiple postures detectable, e.g., by posture sensor 51. In some examples, the target posture may be defined as any posture that is not defined as an undesirable posture. For example, processing circuitry 40 may withhold the delivery of defibrillation shocks if patient is occupying one or more particular posture that is defined as undesirable (e.g., an upright/standing posture or reclined posture) and delivery defibrillation shock(s) as described in FIG. 6 if patient occupies any posture (defined or undefined) that is different than the defined undesirable/non-targeted posture(s).

Experimental Results

This disclosure includes the following discussion which forms part of this disclosure, and may provide many details and examples consistent with this disclosure. As described further below, one or more studies and experiments were carried out to evaluate one or more aspects of example of the disclosure. However, the disclosure is not limited by the studies and experiments. Certain aspect of the studies and experiments are described further below. The details and examples of the following discussion may quantify variation of cardiac signal sensing by an extra-vascular ICD (EV-ICD), like IMD 12, based on respiration and posture. The modeling in such examples may similarly be used quantify variation in anti-tachyarrhythmia shock parameters desired in response to varying posture and respiration states to achieve therapeutic benefit with efficient use of power resources.

Acute human clinical studies have been completed which evaluate substernal therapy delivery and modeling efforts have been aimed at predicting chronic electrical performance for EV ICD. For example, electrophysiological modeling was used to evaluate defibrillation thresholds (DFTs) against a variety of can positions (e.g., cranial versus caudal and anterior versus posterior), as well as against posture changes and respiration. The following discussion describes example of methods in the context of sensing used for modeling. The same models used for defibrillation (and pacing) except that the electrodes are the sources of driving potential instead of the surface of the heart.

In some examples, an EV ICD uses a defibrillation lead placed outside the heart in the anterior mediastinal space. In that location, the electrodes may have some freedom of movement relative to the heart with changing posture. The degree of influence of this motion on electrograms acquired via electrodes in this novel implant location have not been systematically characterized. Studies were carried out to quantify the variation in sensed signals due to changes in posture and respiration.

A first modeling study used sets of MRI scans acquired in various postures and respiratory states to derive anthropometric data quantifying organ motion and shape relative to a supine, end inhalation posture representative of the implant condition. Detailed data for critical anatomy, such as the heart and epicardial fat, was obtained from high resolution ex vivo MM scans and fused with the lower resolution MRIs to create anatomies with appropriate levels of detail for accurate simulation. Matched sets of computational meshes were created, representing a subject in various poses, and then the ICD is "implanted" multiple times in matched positions across these postures. Epicardial potentials were separately estimated from body surface recordings and mapped onto the myocardial surface.

Figure 9:
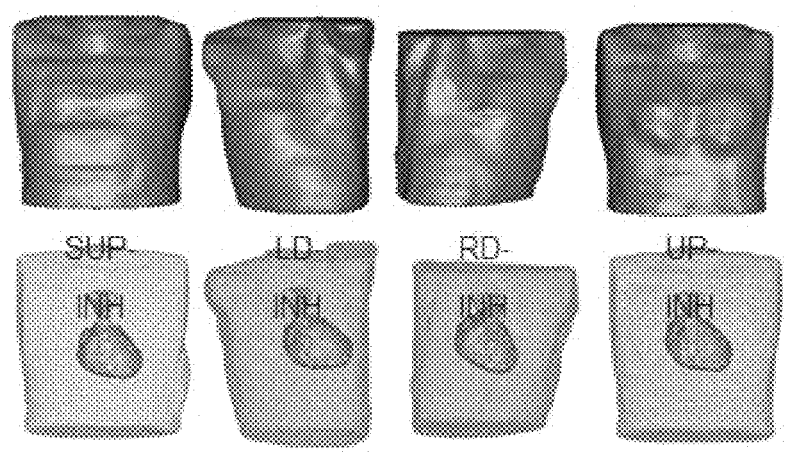
FIG. 9 is a diagram illustrating four MRI scans (top) and corresponding models (bottom) showing the location of a patient's heart within the patient.

FIG. 9 is a diagram illustrating four MRI scans (top) and corresponding models (bottom) showing the location of a patient's heart within the patient (e.g, within the thoracic cavity) at inhalation (INH) of the patient in a supine (SUP), lying down on left side (LD), lying down on right side (RD), and upright (UP) posture. As shown, the relative position of the patient's heart was different for each the different postures. In one patient, 20 mm cranial/caudal movement of the heart was observed during tidal breathing and 60 mm of movement was observed during deep breathing.

The epicardial potential data was manually annotated with scoring windows identifying various types of beats such as normal sinus rhythm (NSR) or ventricular tachycardia (VT). An automated system computed the cardiac signals at the ICD's electrodes for more than 2000 datasets, scores them automatically and stores these results in a database for statistical analysis.

Figure 10:
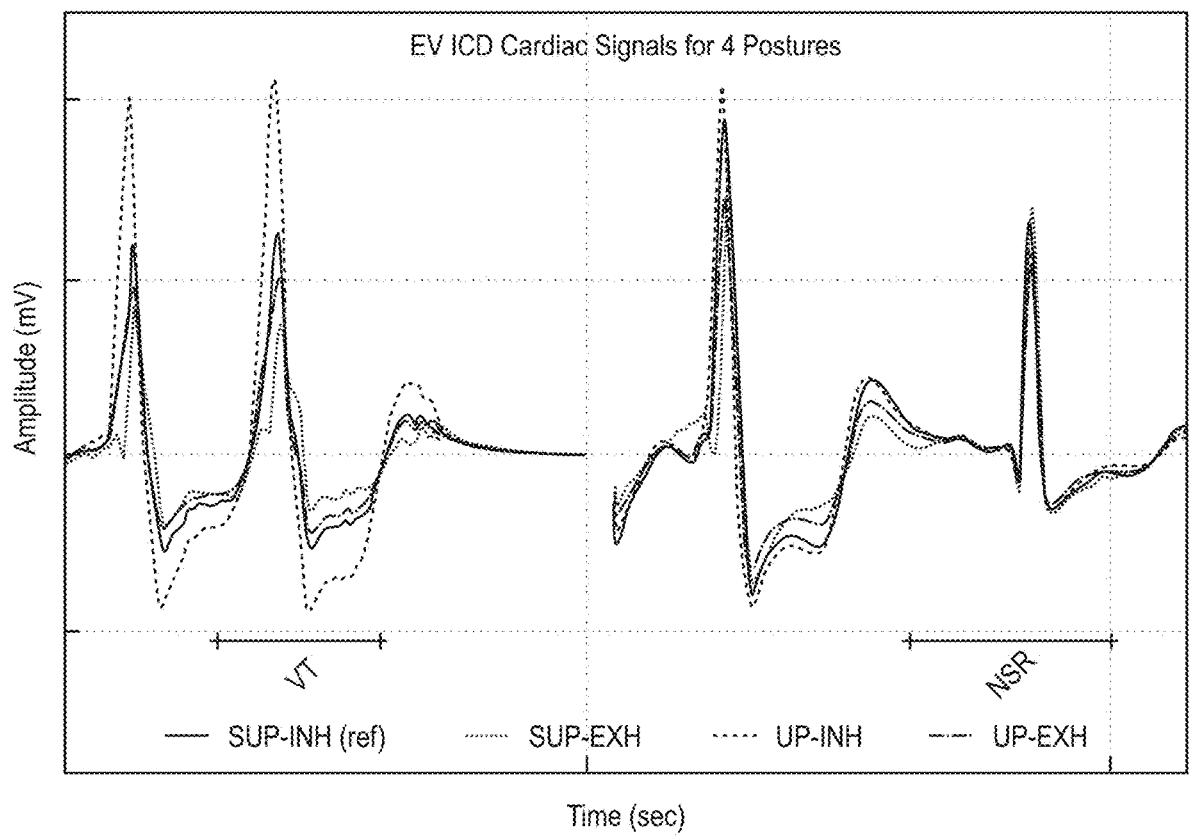
FIG. 10 is a plot of EV ICD cardiac signals for four postures of a patient.

From the motion analysis of the MRI image data it was found that the average cranial-caudal motion of the heart apex was 34 mm (range: 3 to 70 mm, N=9). An example of the predicted signal, with scoring windows, is shown in the FIG. 10 for four combinations of the supine (SUP), upright (UP), inhalation (INH) and exhalation (EXH) denoted by SUP-INH, SUP-EXH, UP-INH and UP-EXH. In this single example, the baseline to peak amplitude, in millivolts (mVpk) for an NSR complex ranges from 1.46 to 2.09 mVpk while a VT complex ranges from 0.75 to 2.22 mVpk. For both complexes the minimum amplitude is associated with the supine, exhalation posture (SUP-EXH) and the maximum amplitude is for the upright, inhalation posture (UP-INH).

Results from the modelling were useful to assess both signal amplitude and postural stability. The results were also used to test guidelines for device and lead implant locations to assure adequate signal levels in all postures for successful arrhythmia detection. The inclusion of postural variation is essential for assuring ambulatory performance of an EV ICD with electrodes outside the heart.

Figure 11A:
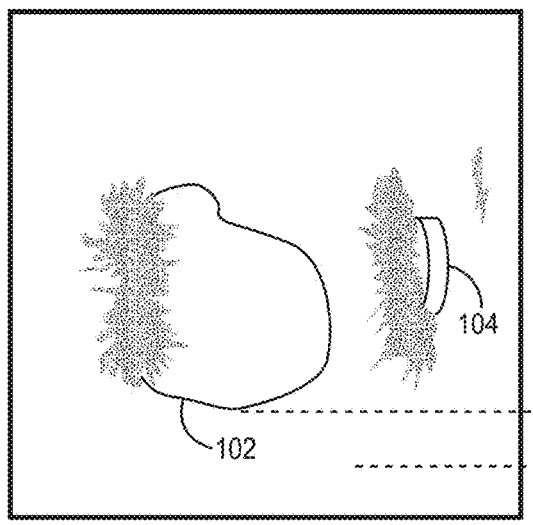
FIGS. 11A and 11B are conceptual illustrations of MRI images of a patient's heart in a supine posture (FIG. 11A) and an upright posture (FIG. 11B) during inhalation along with an EV ICD.
Figure 11B:
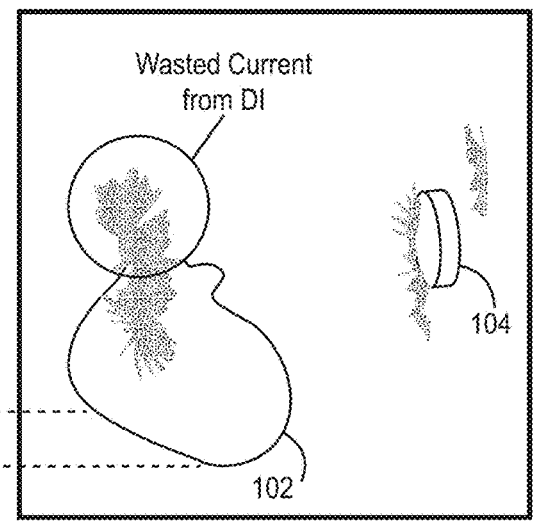

FIGS. 11A and 11B are conceptual illustrations of MRI images of a patient's heart 102 in a supine posture (FIG. 11A) and an upright posture (FIG. 11B) during inhalation along with an EV ICD 104. The shaded areas in both FIGS. 11A and 11B indicate areas of high current density from the delivery of defibriallation therapy using defibrillation vector D1, which includes an a housing electrode in combination with at least one lead electrode. As shown, upon standing and during inhalation, heart 102 moved cadually as indicated by the arrow between the images. In some examples, this may result in the defibrillation vector D1 becoming less effective during defibrillation. As such, for some cases, the defibrillation efficacy may be improved by sensing the upright posture and, in response to sensing the upright posture, disabling a vector (e.g., vector D1), increasing the defibrillation energy, or both.

Figure 12:
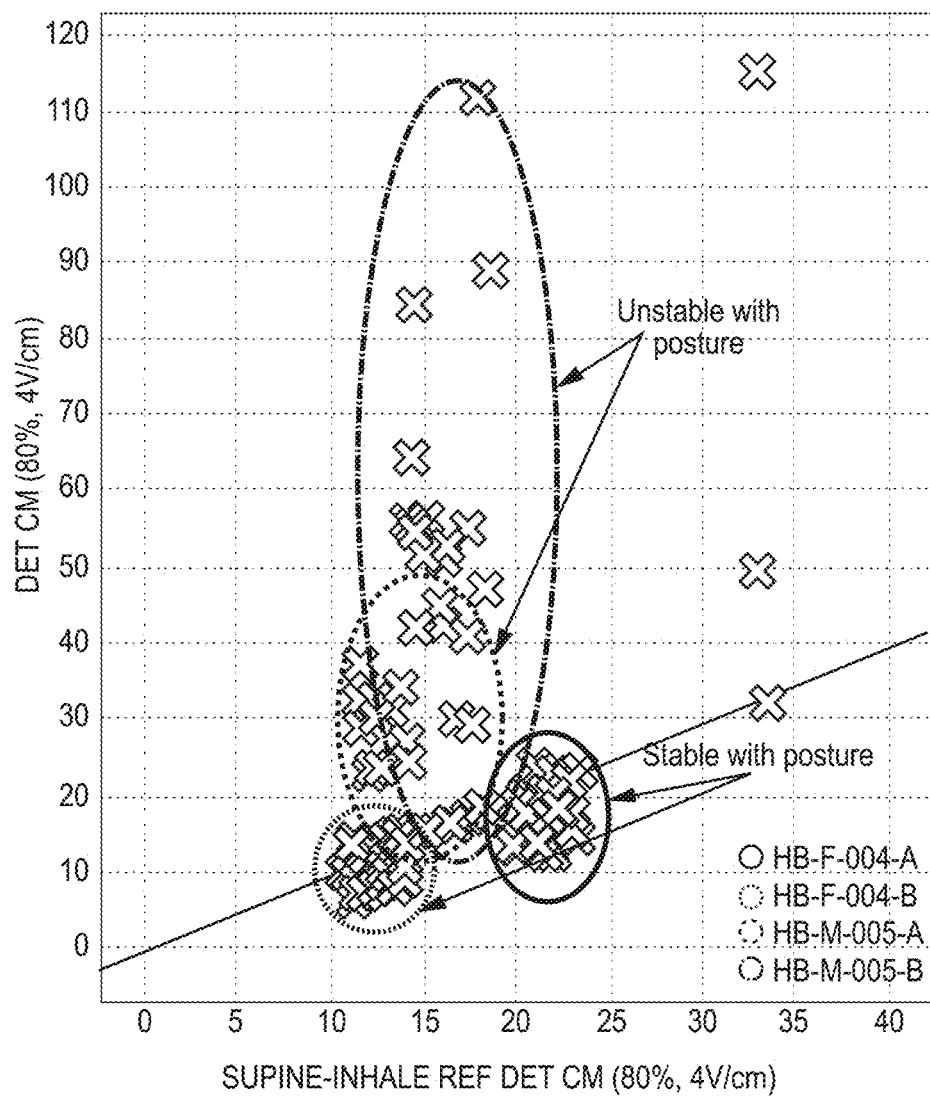
FIG. 12 is a graph illustrating DFT variation with posture and respiration for a variety of modelled patients.

FIG. 12 is a graph illustrating DFT variation with posture and respiration for a variety of modelled patients. The stability graph compares defibrillation threshold (DFT) in the supine, inhalation case (X axis) with the value in all other postures (Y axis). For some patients (HB-F-004-A and HB-F-004-B) the DFT was stable versus posture while for others (HB-M-005-A and HB-M-005-B) it may vary widely. It was believed that patients with an unstable DFT may benefit from a device that increases shock energy when the patient is sensed to be in a posture that has been determined to be problematic.

Surprisingly, aspects of the modeling work revealed that DFT is affected by respiratory cycle, with lowest predicted DFTs coinciding with end tidal exhalation for a given can placement or patient posture. Results from the electrophysiological modeling are presented in FIGS. 7 and 8.

Figure 7:
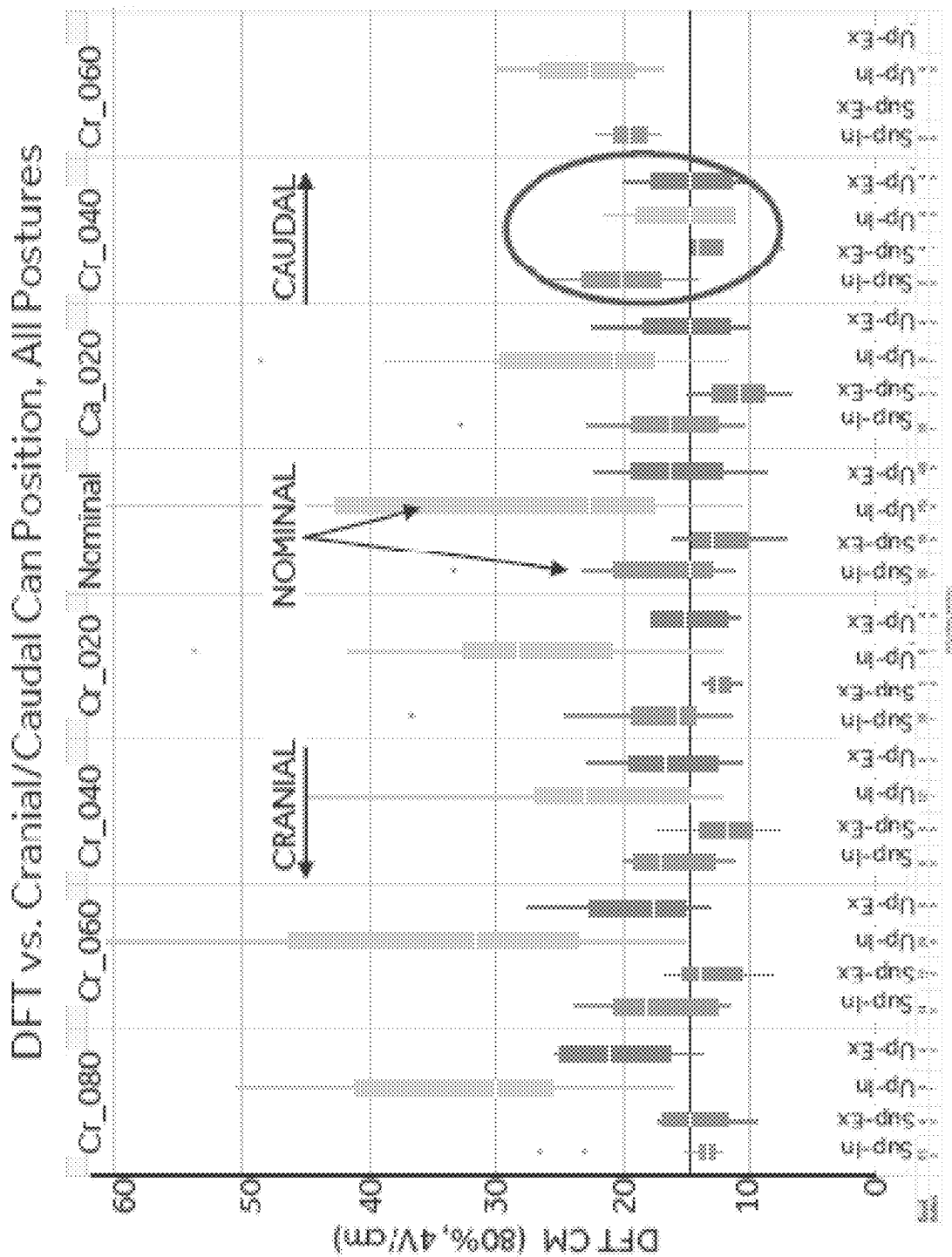
FIG. 7 is a plot of defibrillation thresholds (DFTs) versus various combinations of IMD positions within a patient and respiration phases of the patient.

FIG. 7 is a plot of DFT for nominal lead and various IMD housing (can electrode) implant positions within the modeled patient and patient postures. For the modeling, the IMD housing was positioned generally in subcutaneously on the left side of the patient above the ribcage and the defibrillation electrode positioned substernally, as described above. In the plot, the nominal IMD housing implant position is labelled in approximately the horizontal center with the modeled position moving caudally from the nominal position in increments of 20 mm as the plot moves right and moving cranially from the nominal position in increments of 20 mm as the plot moves left. For each implant location, the DFT was determined for the modeled condition of the patients in the supine posture and at approximately the end of an inhale ("Sup-In"), in the supine posture and at approximately the end of an exhale ("Sup-Ex"), in the upright/standing posture and at approximately the end of an inhale ("Up-In"), and in the upright/standing posture and at approximately the end of an exhale ("Up-Ex").

Based on the results displayed in the plot of FIG. 7, it was determined although the nominal position was advantageous for the Sup-In case in terms of DFT, Sup-In was relatively unstable for Up-In in terms of variability of DFT. Both the Sup-In and Up-In are labelled in FIG. 7. It was also determined that a more caudal placement of the IMD housing improved stability in terms of DFT variability in both cases for a small increase in DFT in the Sup-In case.

As shown in FIG. 7, for each of the IMD housing positions, the DFT was generally lower for the approximate end of an exhale in each of the upright/standing posture and supine position case compared to the same postures but at approximately the end of inhale. Further, the DFT for Sup-Ex was lower for the majority of the IMD housing positions compared to the other three cases. For all of the subjects, end exhalation was determined to be the best state for delivering defibrillation shocks.

Figure 8:
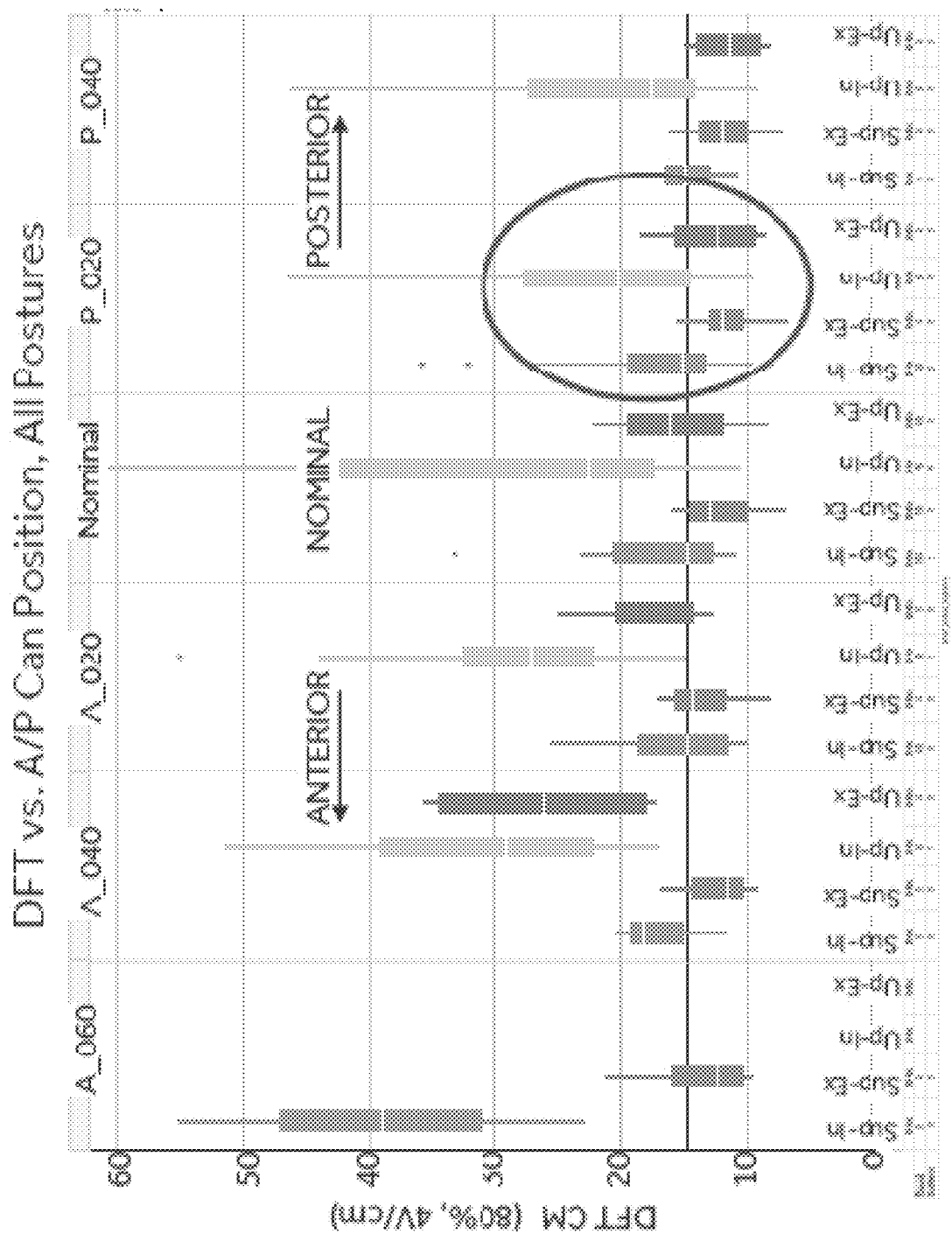
FIG. 8 is another plot of DFTs versus various combinations of IMD positions within a patient and respiration phases of the patient.

FIG. 8 is a plot of DFT for nominal lead and various IMD housing (can electrode) implant positions within the modeled patient and patient postures. For the modeling, the IMD housing was positioned generally in subcutaneously on the left side of the patient above the ribcage and the defibrillation electrode positioned substernally, as described above. In the plot, the nominal IMD housing implant position is labelled in approximately the horizontal center with the modeled position moving posteriorly from the nominal position in increments of 20 mm as the plot moves right and moving anteriorly from the nominal position in increments of 20 mm as the plot moves left. For each implant location, the DFT was determined for the modeled condition of the patients in the supine posture and at approximately the end of an inhale ("Sup-In"), in the supine posture and at approximately the end of an exhale ("Sup-Ex"), in the upright/standing posture and at approximately the end of an inhale ("Up-In"), and in the upright/standing posture and at approximately the end of an exhale ("Up-Ex").

Based on the results displayed in the plot of FIG. 8, it was determined that the nominal IMD housing position was good for Sup-In in terms of relatively low DFT but is the most unstable position in terms of variability. Additionally, the results plotted in FIG. 8 indicated that a more posterior placement of 20 mm to 40 mm from the nominal position improved stability in terms of DFT variability.

Although processing circuitry 40 of IMD 12 is described above as being configured to perform one or more of the steps of the techniques described with respect to FIGS. 1-6, any steps of the techniques described herein may be performed by processing circuitry of the other devices. For example, processing circuitry of a remote computer located with a clinician, or of any other suitable implantable or external device or server, may be configured to perform one or more of the steps described as being performed by processing circuitry 40 of IMD 12. Such other implantable or external devices may include, for example, an implantable or external monitoring device, or any other suitable device.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the terms "processor" or "processing circuitry" as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims and clauses.

Clause 1. A method comprising identifying a time at which a respiratory volume of a lung of a patient is at approximately end tidal volume or less; and delivering, via a medical device system, an anti-tachyarrhythmia shock to a heart of the patient at the time that the respiratory volume of the lung of a patient is at the approximately end tidal volume or less.

Clause 2. The method of clause 1, further comprising monitoring a respiration of the lung of the patient over a time period prior to delivery of the anti-tachyarrhythmia shock, wherein the time at which a respiratory volume of a lung of a patient is at approximately end tidal volume or less is identified based at least in part on the monitored respiratory cycle of the lung of the patient.

Clause 3. The method of clauses 1 or 2, wherein identifying the time at which the respiratory volume of a lung of a patient is at approximately end tidal volume or less comprises identifying an approximate end of an exhalation of the patient.

Clause 4. The method of clause 3, wherein delivering the anti-tachyarrhythmia shock to a heart of the patient at the time that the respiratory volume of the lung of a patient is at the approximately end tidal volume or less comprises delivering the anti-tachyarrhythmia shock to the heart of the patient to substantially coincide with the approximate end of the exhalation of the patient.

Clause 5. The method of any of clauses 1-4, further comprising detecting a ventricular fibrillation (VF) or ventricular tachycardia (VT) of the heart of the patient via the implantable medical device, wherein delivering the anti-tachyarrhythmia shock comprises delivering the anti-tachyarrhythmia shock in response to detecting the VF or VT.

Clause 6. The method of claim 5, wherein identifying the time at which the respiratory volume of a lung of the patient is at approximately end tidal volume or less comprises identifying the time at which the respiratory volume of the lung of the patient is at approximately end tidal volume or less in response to detecting the VF or the VT of the heart of the patient.

Clause 7. The method of clause 5, wherein detecting the ventricular fibrillation (VF) or the ventricular tachycardia (VT) of the heart of the patient via the medical device comprises detecting the ventricular fibrillation (VF) or the ventricular tachycardia (VT) of the heart of the patient via the medical device when the respiratory volume of the lung of the patient is greater than the approximately end tidal volume.

Clause 8. The method of clause 5, further comprising determining that the respiratory volume of the lung of the patient is greater than the approximately end tidal volume in response to detecting the ventricular fibrillation (VF) or the ventricular tachycardia (VT) of the heart of the patient; and delaying the delivery of the anti-tachyarrhythmia shock to the heart of the patient until the time that the respiratory volume of the lung of a patient is at the approximately end tidal volume or less.

Clause 9. The method of any of clauses 1-8, further comprising determining a posture occupied by the patient at the time at which the respiratory volume of the lung of the patient is at approximately end tidal volume or less is a target posture, wherein delivering the anti-tachyarrhythmia shock to the heart of the patient at the time that the respiratory volume of the lung of the patient is at the approximately end tidal volume or less comprises delivering the anti-tachyarrhythmia shock to the heart of the patient at the time that the respiratory volume of the lung of the patient is at the approximately end tidal volume or less and the patient occupies the target posture.

Clause 10. The method of any of clauses 1-9, further comprising determining a posture occupied by the patient at the time at which the respiratory volume of the lung of the patient is at approximately end tidal volume or less is not a target posture, delaying, in response to the determination that the posture of the patient is not the target posture, the delivery of the anti-tachyarrhythmia shock to the heart of the patient at the time that the respiratory volume of the lung of the patient is at the approximately end tidal volume or less.

Clause 11. The method of any of clauses 9 and 10, wherein the target posture of the patient is a lying posture.

Clause 12. The method of any of clauses 9 and 10, wherein the target posture of the patient is a supine posture.

Clause 13. The method of any of clauses 1-12, wherein identifying the time at which the respiratory volume of the lung of the patient is at approximately end tidal volume or less comprises identifying a time at which the respiratory volume of the lung of the patient is at end tidal volume or less.

Clause 14. The method of any of clauses 1-12, wherein identifying the time at which the respiratory volume of the lung of the patient is at approximately end tidal volume or less comprises identifying a time at which the respiratory volume of the lung of the patient is at approximately end tidal volume.

Clause 15. The method of any of clauses 1-12, wherein identifying the time at which the respiratory volume of the lung of the patient is at approximately end tidal volume or less comprises identifying a time at which the respiratory volume of the lung of the patient is about 50% of a tidal volume of the lung of the patient or less.

Clause 16. The method of any of clauses 1-12, wherein identifying the time at which the respiratory volume of the lung of the patient is at approximately end tidal volume or less comprises identifying a time at which the respiratory volume of the lung of the patient is within about 5 seconds from an end of exhalation of the lung of the patient.

Clause 17. The method of any of clauses 1-12, wherein identifying the time at which the respiratory volume of the lung of the patient is at approximately end tidal volume or less comprises identifying a time at which the respiratory volume of the lung of the patient is about 5 seconds following the end if an inhalation of the lung of the patient.

Clause 18. The method of any of clauses 1-17, wherein delivering the anti-tachyarrhythmia shock to the heart of the patient at the time that the respiratory volume of the lung of a patient is at the approximately end tidal volume or less comprises delivering a anti-tachyarrhythmia shock to the heart of the patient at approximately an end of an exhalation of the lung of the patient.

Clause 19. The method of any of clauses 1-17, wherein delivering the anti-tachyarrhythmia shock to the heart of the patient at the time that the respiratory volume of the lung of a patient is at the approximately end tidal volume or less comprises delivering a anti-tachyarrhythmia shock to the heart of the patient at an end of an exhalation of the lung of the patient.

Clause 20. The method of any of clauses 1-19, wherein the medical device system includes an implantable medical device system including an implantable medical device.

Clause 21. The method of clause 20, wherein the implantable medical device system includes an extravascular implantable cardiac device system.

Clause 22. The method of clause 20, wherein the extravascular implantable cardiac device system includes a lead including one or more electrodes configured to deliver the anti-tachyarrhythmia shock, wherein the one or more electrodes are at a substernal and extravascular location within the patient.

Clause 23. The method of any of clauses 1-22, wherein the anti-tachyarrhythmia shock comprises one or more defibrillation shocks.

Clause 24. The method of any of clauses 1-22, wherein the anti-tachyarrhythmia shock comprises one or more cardioversion shocks.

Clause 25. A method comprising determining an approximate end of exhalation by a patient; and delivering, via a medical device system, an anti-tachyarrhythmia shock to a heart of the patient substantially coincidentally with the approximate end of exhalation by a patient based on the determination.

Clause 26. A medical device system comprising therapy generation circuitry configured to generate an anti-tachyarrhythmia shock; and processing circuitry configured to identify a time at which a respiratory volume of a lung of a patient is at approximately end tidal volume or less; and control the therapy generation circuitry to deliver the anti-tachyarrhythmia shock to a heart of the patient at the time that the respiratory volume of the lung of a patient is at the approximately end tidal volume or less.

Clause 27. The medical device system of clause 26, wherein the medical device system is configured to perform any method of clause 1-25.

Clause 28. A method comprising any method described herein, or any combination of the methods described herein.

Clause 29. A method comprising any combination of the methods of clauses 1-25.

Clause 30. A system comprising means for performing the method of any of clauses 1-25.

Clause 31. A non-transitory computer-readable storage medium comprising instructions stored thereon that, when executed by processing circuitry cause the processing circuitry to perform the method of any of clauses 1-25.

Clause 32. A method comprising identifying a time at which a respiratory volume of a lung of a patient is at approximately end tidal volume or less; and delivering, via a medical device system, an anti-tachyarrhythmia therapy to a heart of the patient at the time that the respiratory volume of the lung of a patient is at the approximately end tidal volume or less.

Claim 33. The method of clause 32, wherein delivering the anti-tachyarrhythmia therapy comprises delivering one or more of defibrillation shock(s), cardioversion shock(s), antitachycardia pacing (ATP), post shock pacing, or bradycardia pacing.

Clause 34. A system comprising therapy generation circuitry configured to generate an anti-tachyarrhythmia therapy; and processing circuitry configured to identify a time at which a respiratory volume of a lung of a patient is at approximately end tidal volume or less; and control the therapy generation circuitry to deliver the anti-tachyarrhythmia therapy to a heart of the patient at the time that the respiratory volume of the lung of a patient is at the approximately end tidal volume or less.

Clause 35. The system of clause 35, wherein the anti-tachyarrhythmia therapy comprises one or more of defibrillation shock(s), cardioversion shock(s), antitachycardia pacing (ATP), post shock pacing, or bradycardia pacing.

The invention claimed is:

1. A method comprising:
    detecting a ventricular fibrillation (VF) or ventricular tachycardia (VT) of a heart of a patient via a medical device;
    identifying, following the VF or VT of the heart of the patient, a first time at which a respiratory volume of a lung of the patient is at approximately end tidal volume or less;
    identifying a second time following the first time at which the respiratory volume of the lung of the patient is at approximately end tidal volume or less; and
    delivering, via an implantable medical device, an anti-tachyarrhythmia shock to the heart of the patient at the second time that the respiratory volume of the lung of the patient is at the approximately end tidal volume or less but not at the first time, wherein the anti-tachyarrhythmia shock is delivered substantially coincidentally with an approximate end of an exhalation by patient.

2. The method of claim 1, further comprising monitoring a respiration of the lung of the patient over a time period prior to delivery of the anti-tachyarrhythmia shock, wherein the second time at which the respiratory volume of the lung of the patient is at the approximately end tidal volume or less is identified based at least in part on the monitored respiratory cycle of the lung of the patient.

3. The method of claim 1, wherein at least one of the identifying the first time at which the respiratory volume of the lung of a patient is at the approximately end tidal volume or less or the identifying the second time at which the respiratory volume of the lung of the patient is at the approximately end tidal volume or less comprises identifying the approximate end of the exhalation of the patient.

4. The method of claim 1, wherein delivering the anti-tachyarrhythmia shock comprises delivering the anti-tachyarrhythmia shock in response to detecting the VF or VT.

5. The method of claim 4, wherein identifying the second time at which the respiratory volume of the lung of the patient is at the approximately end tidal volume or less comprises identifying the second time at which the respiratory volume of the lung of the patient is at the approximately end tidal volume or less in response to detecting the VF or the VT of the heart of the patient.

6. The method of claim 4, wherein detecting the ventricular fibrillation (VF) or ventricular tachycardia (VT) of the heart of the patient via the medical device comprises detecting the ventricular fibrillation (VF) or the ventricular tachycardia (VT) of the heart of the patient via the medical device when the respiratory volume of the lung of the patient is greater than the approximately end tidal volume.

7. The method of claim 4, further comprising:
    determining that the respiratory volume of the lung of the patient is greater than the approximately end tidal volume in response to detecting the ventricular fibrillation (VF) or the ventricular tachycardia (VT) of the heart of the patient; and
    delaying the delivery of the anti-tachyarrhythmia shock to the heart of the patient until the second time that the respiratory volume of the lung of the patient is at the approximately end tidal volume or less.

8. The method of claim 1, further comprising determining a posture occupied by the patient at the second time at which the respiratory volume of the lung of the patient is at the approximately end tidal volume or less is a target posture, wherein delivering the anti-tachyarrhythmia shock to the heart of the patient at the second time that the respiratory volume of the lung of the patient is at the approximately end tidal volume or less comprises delivering the anti-tachyarrhythmia shock to the heart of the patient at the second time that the respiratory volume of the lung of the patient is at the approximately end tidal volume or less and the patient occupies the target posture.

9. An implantable medical device system comprising:
    therapy generation circuitry configured to generate an anti-tachyarrhythmia shock; and
    processing circuitry configured to:
        detect a ventricular fibrillation (VF) or ventricular tachycardia (VT) of a heart of a patient,
        identify, following the VF or VT of the heart of the patient, a first time at which a respiratory volume of a lung of the patient is at approximately end tidal volume or less,
        identify a second time following the first time at which the respiratory volume of the lung of the patient is at approximately end tidal volume or less and
        control the therapy generation circuitry to deliver the anti-tachyarrhythmia shock to the heart of the patient at the second time that the respiratory volume of the lung of the patient is at the approximately end tidal volume or less but not at the first time, wherein the processing circuitry is configured to control the therapy generation circuitry to deliver the anti-tachyarrhythmia shock to the heart of the patient to substantially coincide with the approximate end of the exhalation of the patient.

10. The system of claim 9, wherein the processing circuitry is configured to:
    monitor a respiration of the lung of the patient over a time period prior to delivery of the anti-tachyarrhythmia shock, and
    identify the second time at which the respiratory volume of the lung of the patient is at the approximately end tidal volume or less based at least in part on the monitored respiratory cycle of the lung of the patient.

11. The system of claim 9, wherein the processing circuitry is configured to identify the approximate end of the exhalation of the patient to at least one of identify the first time at which the respiratory volume of the lung of a patient is at the approximately end tidal volume or less or identify the second time at which the respiratory volume of the lung of the patient is at the approximately end tidal volume or less.

12. The system of claim 9, wherein the processing circuitry is configured to control the therapy generation circuitry to deliver the anti-tachyarrhythmia shock in response to detecting the VF or VT.

13. The system of claim 12, wherein the processing circuitry is configured to identify the second time at which the respiratory volume of the lung of the patient is at the approximately end tidal volume or less in response to detecting the VF or the VT of the heart of the patient.

14. The system of claim 12, wherein the processing circuitry is configured to detect the ventricular fibrillation (VF) or the ventricular tachycardia (VT) of the heart of the patient via the medical device when the respiratory volume of the lung of the patient is greater than the approximately end tidal volume.

15. The system of claim 12, wherein the processing circuitry is configured to:
  determine that the respiratory volume of the lung of the patient is greater than the approximately end tidal volume in response to detecting the ventricular fibrillation (VF) or the ventricular tachycardia (VT) of the heart of the patient; and
  control the therapy generation circuitry to delay the delivery of the anti-tachyarrhythmia shock to the heart of the patient until the second time that the respiratory volume of the lung of the patient is at the approximately end tidal volume or less.

16. The system of claim 9, wherein the processing circuitry is configured to:
  determining a posture occupied by the patient at the second time at which the respiratory volume of the lung of the patient is at the approximately end tidal volume or less is a target posture, and
  control the therapy generation circuitry to deliver the anti-tachyarrhythmia shock to the heart of the patient at the second time that the respiratory volume of the lung of the patient is at the approximately end tidal volume or less and the patient occupies the target posture.

17. The system of claim 9, further comprising an implantable acoustic sensor configured to generate a signal indicative of the respiratory volume of the patient, wherein the processing circuitry is configured to identify the first time and the second time at which the respiratory volume of the lung of the patient is at approximately end tidal volume or less based on the signal generated by the acoustic sensor.

18. The system of claim 9, further comprising a movement sensor configured to generate a signal indicative of the respiratory volume of the patient, wherein the processing circuitry is configured to identify the first time and the second time at which the respiratory volume of the lung of the patient is at approximately end tidal volume or less based on the signal generated by the movement sensor.

19. The system of claim 9, further comprising an implantable pressure sensor configured to generate a signal indicative of the respiratory volume of the patient, wherein the processing circuitry is configured to identify the first time and the second time at which the respiratory volume of the lung of the patient is at approximately end tidal volume or less based on the signal generated by the pressure sensor.

20. The system of claim 19, further comprising an implantable medical lead, wherein the therapy generation circuitry is configured to deliver the anti-tachyarrhythmia shock to the heart of the patient via at least one electrode on the implantable medical lead, and wherein the implantable pressure sensor is located on the implantable medical lead.

21. The system of claim 9, further comprising an implantable cardiac electrogram (EGM) sensor configured to generate a signal indicative of the respiratory volume of the patient, wherein the processing circuitry is configured to identify the first time and the second time at which the respiratory volume of the lung of the patient is at approximately end tidal volume or less based on the signal generated by the cardiac EGM sensor.

22. The system of claim 9, further comprising an implantable cardiac device configured to be implanted in the patient, the implantable cardiac device including the therapy generation circuitry and the processing circuitry, wherein the implantable cardiac device is configured to deliver the anti-tachyarrhythmia shock to the heart of the patient via one or more electrodes implanted in the patient.

23. A method comprising:
  identifying at least one time at which a respiratory volume of a lung of a patient is at approximately end tidal volume or less;
  determining a posture occupied by the patient at the at least one time at which the respiratory volume of the lung of the patient is at the approximately end tidal volume or less is not a target posture;
  delaying, in response to the determination that the posture of the patient is not the target posture, delivery of an anti-tachyarrhythmia shock to a heart of the patient at the at least one time that the respiratory volume of the lung of the patient is at the approximately end tidal volume or less until the patient occupies the target posture; and
  subsequently delivering, via an implantable medical device, the anti-tachyarrhythmia shock to the heart of the patient at the at least one time that the respiratory volume of the lung of the patient is at the approximately end tidal volume or less and the patient occupies the target posture.

24. The method of claim 23, wherein the target posture of the patient is one of a lying posture or a supine posture.

25. A medical device system comprising an implantable medical device comprising:
  therapy generation circuitry configured to generate an anti-tachyarrhythmia shock; and
  processing circuitry configured to:
    identify at least one time at which a respiratory volume of a lung of a patient is at approximately end tidal volume or less,
    determine a posture occupied by the patient at the at least one time at which the respiratory volume of the lung of the patient is at the approximately end tidal volume or less is not a target posture,
    control the therapy generation circuitry to delay, in response to the determination that the posture of the patient is not the target posture, delivery of the anti-tachyarrhythmia shock to a heart of the patient at the at least one time that the respiratory volume of the lung of the patient is at the approximately end tidal volume or less until the patient occupies the target posture, and
    subsequently control the delivery of the anti-tachyarrhythmia shock to the heart of the patient at the at least one time that the respiratory volume of the lung of the patient is at the approximately end tidal volume or less and the patient occupies the target posture.

26. The system of claim 25, wherein the target posture of the patient is one of a lying posture or a supine posture.

* * * * *